US011185700B2

(12) United States Patent
Ternes et al.

(10) Patent No.: US 11,185,700 B2
(45) Date of Patent: Nov. 30, 2021

(54) SYSTEMS AND METHODS FOR DYNAMIC CONTROL OF HEART FAILURE THERAPY

(71) Applicant: Cardiac Pacemakers, Inc., St. Paul, MN (US)

(72) Inventors: David J. Ternes, Roseville, MN (US); Yinghong Yu, Shoreview, MN (US); Jason Humphrey, New Brighton, MN (US); David L. Perschbacher, Coon Rapids, MN (US); Michael James Dufresne, Lino Lakes, MN (US); Adam MacEwen, White Bear Lake, MN (US); Keith L. Herrmann, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 542 days.

(21) Appl. No.: 16/007,784

(22) Filed: Jun. 13, 2018

(65) Prior Publication Data

US 2018/0361161 A1 Dec. 20, 2018

Related U.S. Application Data

(60) Provisional application No. 62/521,215, filed on Jun. 16, 2017.

(51) Int. Cl.
*A61N 1/365* (2006.01)
*A61N 1/368* (2006.01)
(Continued)

(52) U.S. Cl.
CPC ....... *A61N 1/36585* (2013.01); *A61N 1/3627* (2013.01); *A61N 1/3682* (2013.01);
(Continued)

(58) Field of Classification Search
CPC .............. A61N 1/3956; A61N 1/36585; A61N 1/36842; A61N 1/36843; A61N 1/3627;
(Continued)

(56) References Cited

U.S. PATENT DOCUMENTS 5,340,361 A 8/1994 Sholder
5,527,347 A 6/1996 Shelton et al.
(Continued)

FOREIGN PATENT DOCUMENTS

AU 2018285868 B2 11/2020
CN 110740780 A 1/2020
(Continued)

OTHER PUBLICATIONS

Daubert, Jean-Claude, et al., "2012 EHRA/HRS expert consensus statement on cardiac resynchronization therapy in heart failure: implant and follow-up recommendations and management", Heart Rhythm, vol. 9, No. 9, Sep. 2012, pp. 1524-1576.
(Continued)

*Primary Examiner* — Lindsey G Wehrheim
(74) *Attorney, Agent, or Firm* — Schwegman Lundberg & Woessner, P.A.

(57) ABSTRACT

Systems and methods for monitoring and treating patients with heart failure (HF) are discussed. The system may sense cardiac signals, and receives information about patient physiological or functional conditions. A stimulation parameter table that includes recommended values of atrioventricular delay (AVD) or other timing parameters maybe created at a multitude of patient physiological or functional conditions. The system may periodically reassess patient physiological or functional conditions. A therapy programmer circuit may dynamically switch between left ventricular-only pacing and biventricular pacing, or switch between single site pacing and multisite pacing based on the patient
(Continued)

condition. The therapy programmer circuit may adjust AVD and other timing parameters using the cardiac signal input and the stored stimulation parameter table. A HF therapy may be delivered according to the determined stimulation site, stimulation mode, and the stimulation timing.

20 Claims, 8 Drawing Sheets

(51) Int. Cl.
*A61N 1/37* (2006.01)
*A61N 1/362* (2006.01)
*A61N 1/372* (2006.01)
*A61N 1/378* (2006.01)
*A61N 1/39* (2006.01)
*A61B 5/029* (2006.01)

(52) U.S. Cl.
CPC ......... *A61N 1/3686* (2013.01); *A61N 1/3688* (2013.01); *A61N 1/36535* (2013.01); *A61N 1/36571* (2013.01); *A61N 1/36592* (2013.01); *A61N 1/36842* (2017.08); *A61N 1/36843* (2017.08); *A61N 1/3702* (2013.01); *A61N 1/3714* (2013.01); *A61N 1/3787* (2013.01); *A61N 1/37264* (2013.01); *A61N 1/3956* (2013.01); *A61B 5/029* (2013.01); *A61N 1/36521* (2013.01); *A61N 1/36542* (2013.01); *A61N 1/36564* (2013.01)

(58) Field of Classification Search
CPC ............ A61N 1/36535; A61N 1/36571; A61N 1/36592; A61N 1/3682; A61N 1/3686; A61N 1/3688; A61N 1/3702; A61N 1/3714; A61N 1/37264; A61N 1/3787; A61N 1/36521; A61N 1/36542; A61N 1/36564; A61B 5/029
See application file for complete search history.

(56) References Cited

U.S. PATENT DOCUMENTS

| | | | |
|---|---|---|---|
| 6,766,197 B1 | 7/2004 | Levine | |
| 6,928,326 B1 | 8/2005 | Levine | |
| 6,973,350 B1 | 12/2005 | Levine et al. | |
| 7,079,896 B1 | 7/2006 | Park et al. | |
| 7,115,096 B2 | 10/2006 | Siejko et al. | |
| 7,972,275 B2 | 7/2011 | Siejko et al. | |
| 8,048,001 B2 | 11/2011 | Patangay et al. | |
| 8,121,685 B2 | 2/2012 | Ding et al. | |
| 8,160,700 B1* | 4/2012 | Ryu ................... | A61N 1/3627 607/9 |
| 9,220,905 B2 | 12/2015 | Munsterman et al. | |
| 9,345,410 B2 | 5/2016 | Thakur et al. | |
| 9,433,792 B2 | 9/2016 | Rosenberg et al. | |
| 9,622,664 B2 | 4/2017 | An et al. | |
| 9,968,266 B2 | 5/2018 | An et al. | |
| 2005/0131476 A1 | 6/2005 | Kim et al. | |
| 2005/0137632 A1 | 6/2005 | Ding et al. | |
| 2006/0224198 A1 | 10/2006 | Dong et al. | |
| 2007/0179542 A1 | 8/2007 | Prakash et al. | |
| 2007/0191892 A1 | 8/2007 | Mullen et al. | |
| 2010/0069988 A1 | 3/2010 | Ding et al. | |
| 2010/0305646 A1 | 12/2010 | Schulte et al. | |
| 2011/0196440 A1 | 8/2011 | Koh | |
| 2012/0158088 A1 | 6/2012 | Kramer et al. | |
| 2013/0030489 A1 | 1/2013 | Munsterman et al. | |
| 2013/0131750 A1* | 5/2013 | Stadler ................ | A61N 1/3686 607/25 |
| 2013/0268017 A1 | 10/2013 | Zhang et al. | |
| 2014/0277233 A1* | 9/2014 | Ghosh ................. | A61N 1/3684 607/17 |
| 2016/0051823 A1 | 2/2016 | Maile et al. | |
| 2016/0144192 A1 | 5/2016 | Sanghera et al. | |
| 2016/0220357 A1 | 8/2016 | Anand et al. | |
| 2016/0310733 A1 | 10/2016 | Sheldon et al. | |
| 2017/0106191 A1 | 4/2017 | Pei | |
| 2018/0361150 A1 | 12/2018 | Ternes et al. | |
| 2018/0361162 A1 | 12/2018 | Ternes et al. | |
| 2019/0298903 A1 | 10/2019 | Gillberg et al. | |
| 2020/0324120 A1 | 10/2020 | Yu et al. | |
| 2020/0324121 A1 | 10/2020 | Yu et al. | |

FOREIGN PATENT DOCUMENTS

| | | |
|---|---|---|
| CN | 110769893 A | 2/2020 |
| CN | 110769894 A | 2/2020 |
| JP | H10504754 A | 5/1998 |
| JP | 2008538981 A | 11/2008 |
| JP | 2012527957 A | 11/2012 |
| JP | 2020523139 A | 8/2020 |
| JP | 2020523152 A | 8/2020 |
| JP | 2020523153 A | 8/2020 |
| WO | WO-2018189671 A1 | 10/2018 |
| WO | WO-2018231939 A1 | 12/2018 |
| WO | WO-2018231996 A1 | 12/2018 |
| WO | WO-2018232004 A1 | 12/2018 |
| WO | WO-2019144058 A1 | 7/2019 |

OTHER PUBLICATIONS

Ellenbogen, Kenneth A., et al., "Primary Results From the SmartDelay Determined AV Optimization: A Comparison to Other AV Delay Methods Used in Cardiac Resynchronization Therapy (SMART-AV) Trial: A Randonmized Trial Comparing Empirical Echocardiography-Guiled, and Algorithmic . . . ", Circulation, http://circ.ahajournals.org/content/early/2010/11/12/ CIRCULATIONAHA.110.992552, Nov. 12, 2010, 19 pages.
"U.S. Appl. No. 16/007,094, Examiner Interview Summary dated Sep. 25, 2020", 3 pgs.
"U.S. Appl. No. 16/007,094, Final Office Action dated Jul. 24, 2020", 18 pgs.
"U.S. Appl. No. 16/007,094, Non Final Office Action dated Dec. 31, 2019", 17 pgs.
"U.S. Appl. No. 16/007,094, Response filed Mar. 31, 2020 to Non Final Office Action dated Dec. 31, 2019", 14 pgs.
"U.S. Appl. No. 16/007,094, Response filed Sep. 24, 2020 to Final Office Action dated Jul. 24, 2020", 13 pgs.
"U.S. Appl. No. 16/007,494, Examiner Interview Summary dated May 15, 2020", 3 pgs.
"U.S. Appl. No. 16/007,494, Non Final Office Action dated Feb. 24, 2020", 16 pgs.
"U.S. Appl. No. 16/007,494, Non Final Office Action dated Sep. 4, 2020", 17 pgs.
"U.S. Appl. No. 16/007,494, Response filed May 26, 2020 to Non Final Office Action dated Feb. 24, 2020", 11 pgs.
"Australian Application Serial No. 2018283029, First Examination Report dated May 7, 2020", 4 pgs.
"Australian Application Serial No. 2018283029, Response filed Aug. 20, 2020, to First Examination Report dated May 7, 2020", 16 pgs.
"Australian Application Serial No. 2018283029, Subsequent Examiners Report dated Oct. 14, 2020", 4 pgs.
"Australian Application Serial No. 2018284386, First Examination Report dated May 11, 2020", 4 pgs.
"Australian Application Serial No. 2018284386, Response filed Aug. 14, 2020 to First Examination Report dated May 11, 2020", 2 pgs.
"Australian Application Serial No. 2018284386, Subsequent Examiners Report dated Sep. 4, 2020", 4 pgs.
"Australian Application Serial No. 2018285868, First Examination Report dated May 6, 2020", 4 pgs.
"Australian Application Serial No. 2018285868, Response filed Sep. 9, 2020 to First Examination Report dated May 6, 2020", 7 pgs.

(56) References Cited

OTHER PUBLICATIONS

"European Application Serial No. 18738066.2, Response to Communication Pursuant to Rules 161 and 162 filed Jul. 28, 2020", 3 pgs.
"European Application Serial No. 18738068.8, Response to Communication Pursuant to Rules 161 and 162 filed Jul. 28, 2020", 16 pgs.
"International Application Serial No. PCT/US2018/037269, International Preliminary Report on Patentability dated Dec. 26, 2019", 8 pgs.
"International Application Serial No. PCT/US2018/037269, International Search Report dated Aug. 31, 2018", 4 pgs.
"International Application Serial No. PCT/US2018/037269, Written Opinion dated Aug. 31, 2018", 6 pgs.
"International Application Serial No. PCT/US2018/037350, International Preliminary Report on Patentability dated Dec. 26, 2019", 9 pgs.
"International Application Serial No. PCT/US2018/037350, International Search Report dated Nov. 16, 2018", 6 pgs.
"International Application Serial No. PCT/US2018/037350, Invitation to Pay Additional Fees and Partial Search Report dated Sep. 20, 2018", 8 pgs.
"International Application Serial No. PCT/US2018/037350, Written Opinion dated Nov. 16, 2018", 7 pgs.
"International Application Serial No. PCT/US2018/037359, International Preliminary Report on Patentability dated Dec. 26, 2019", 8 pgs.
"International Application Serial No. PCT/US2018/037359, International Search Report dated Sep. 18, 2018", 5 pgs.
"International Application Serial No. PCT/US2018/037359, Written Opinion dated Sep. 18, 2018", 8 pgs.
"U.S. Appl. No. 16/007,094, Advisory Action dated Oct. 27, 2020", 4 pgs.
"U.S. Appl. No. 16/007,094, Non Final Office Action dated Jun. 11, 2021", 15 pgs.
"U.S. Appl. No. 16/007,494, Examiner Interview Summary dated Nov. 19, 2020", 4 pgs.
"U.S. Appl. No. 16/007,494, Notice of Allowance dated Feb. 18, 2021", 9 pgs.
"U.S. Appl. No. 16/007,494, Response filed Dec. 7, 2020 to Non Final Office Action dated Sep. 4, 2020", 11 pgs.
"Australian Application Serial No. 2018283029, Response filed Apr. 7, 2021 to Subsequent Examiners Report dated Oct. 14, 2020", 2 pgs.
"European Application Serial No. 18737095.2, Response filed Aug. 4, 2020 to Communication pursuant to Rules 161(1) and 162 EPC dated Jan. 30, 2020", 16 pgs.
"Japanese Application Serial No. 2019-569278, Final Notification of Reasons for Refusal dated Nov. 17, 2020", w/English translation, 12 pgs.
"Japanese Application Serial No. 2019-569278, Response filed Feb. 16, 2021 to Final Notification of Reasons for Refusal dated Nov. 17, 2020", w/ English Claims, 9 pgs.
"Japanese Application Serial No. 2019-569384, Office Action dated Nov. 24, 2020", w/ English translation, 12 pgs.
"Japanese Application Serial No. 2019-569384,Response filed Feb. 22, 2021 Office Action dated Nov. 24, 2020", w/ English Claims, 10 pgs.
"Japanese Application Serial No. 2019-569386, Office Action dated Nov. 24, 2020", w/ English translation, 10 pgs.
"Japanese Application Serial No. 2019-569386, Response Filed Feb. 19, 2021 to Office Action dated Nov. 24, 2020", w/ English Claims, 9 pgs.

* cited by examiner

|  | Supine | | Sitting | | Standing | |
|---|---|---|---|---|---|---|
| HR (bpm) | AS | AP | AS | AP | AS | AP |
| <60 | -- | -- | -- | -- | -- | -- |
| 60-70 | -- | -- | -- | -- | -- | -- |
| 70-80 | -- | -- | -- | -- | -- | -- |
| 80-90 | -- | -- | -- | -- | -- | -- |
| 90-100 | -- | -- | -- | -- | -- | -- |
| >100 | -- | -- | -- | -- | -- | -- |

*FIG. 3A*

|  | Daytime | | Nighttime | |
|---|---|---|---|---|
| HR (bpm) | AS | AP | AS | AP |
| <60 | -- | -- | -- | -- |
| 60-70 | -- | -- | -- | -- |
| 70-80 | -- | -- | -- | -- |
| 80-90 | -- | -- | -- | -- |
| 90-100 | -- | -- | -- | -- |
| >100 | -- | -- | -- | -- |

*FIG. 3B*

SYSTEMS AND METHODS FOR DYNAMIC CONTROL OF HEART FAILURE THERAPY

CLAIM OF PRIORITY

This application claims the benefit of priority under 35 U.S.C. § 119(e) of U.S. Provisional Patent Application Ser. No. 62/521,215, filed on Jun. 16, 2017, which is herein incorporated by reference in its entirety.

TECHNICAL FIELD

This document relates generally to medical systems and devices, and more particularly, to systems, devices, and methods of electrostimulation for treating heart failure.

BACKGROUND

Congestive heart failure (CHF) is a leading cause of death in the United States and globally. CHF occurs when the heart is unable to adequately supply enough blood to maintain a healthy physiological state. CHF may be treated by drug therapy, or by electrostimulation therapy.

Implantable medical devices (IMDs) have been used to monitor CHF patients and manage heart failure in an ambulatory setting. Some IMDs may include sensors to sense physiological signals from a patient, and detect worsening heart failure, such as heart failure decompensation. Frequent patient monitoring and early detection of worsening heart failure may help improve patient outcome. Identification of patient at an elevated risk of future heart failure events may help provide timely treatment and prevent or reduce hospitalization. Identifying and safely managing the patients at risk of worsening heart failure can avoid unnecessary medical interventions, hospitalization, and reduce healthcare cost.

An IMD may include a pulse generator and electrical circuitry configured to electrically stimulate a heart or other excitable tissue, to help restore or improve the cardiac performance, or to correct cardiac arrhythmias. One example of the electrostimulation therapy is cardiac resynchronization therapy (CRT). CRT, typically delivered as biventricular (BiV) pacing or synchronized left ventricle (LV)-only pacing, may be indicated for CHF patients with moderate to severe symptoms and ventricular dyssynchrony. CRT keeps the LV and right ventricle (RV) pumping synchronously by sending electrical stimuli to both the LV and RV. The synchronized stimulation may improve heart pumping efficiency and increase blood flow in some CHF patients. CRT can decrease hospitalization and morbidity associated with worsening heart failure, as well as improvements in quality of life.

SUMMARY

Ambulatory medical devices (AMDs), such as IMDs, subcutaneous medical devices, wearable medical devices, or other external medical devices, may be used to detect worsening heart failure and deliver heart failure (HF) therapy to restore or improve the cardiac function. An IMD may be coupled to implanted leads with electrodes that may be used to sense cardiac activity, or to deliver HF therapy, such as cardiac electrostimulation. An AMD may have functionality of programmable therapy that allows for manual or automatic adjustment of electrostimulation parameters, such as stimulation chamber or site, stimulation mode, or stimulation timing.

An AMD may be configured to stimulation various cardiac chambers to restore cardiac synchrony and improve hemodynamics. During CRT or BiV pacing, synchronized stimulation may be applied to the LV and the RV of a heart. The RV and LV pacing sites may be stimulated simultaneously, or sequentially with an RV-LV interventricular pacing delay (VVD). Delivery of LV and RV pacing may be timed relative to a fiducial point, such as an intrinsic atrial depolarization sensed by an atrial electrode (atrial sense, or AS), or an atrial pacing pulse (AP) that elicits atrial activation. If no intrinsic ventricular depolarization is detected within a period of atrial-ventricular delay (AVD) following the AS or the AP, the LV and RV pacing may be delivered at the end of the AVD.

As an alternative to BiV pacing, stimulation may be delivered only at one heart chamber, such as the LV. Such an LV-only pacing may offer satisfactory synchrony and cardiac performance in certain patients, such as those with intact atrioventricular (AV) conduction requiring cardiac resynchronization. Compared to the BiV pacing, LV-only pacing may require a simpler implantable procedure, consumes less power, and provides increased battery longevity. As such, it is clinically a valid alternative to more complicated BiV therapy regime. Similar to timing of BiV pacing, the LV pacing may be delivered at the end of a programmed AVD subsequent to the AS or the AP if no intrinsic LV depolarization is detected within the period of AVD.

An AMD may be configured to stimulate one or more sites of a heart chamber simultaneously or sequentially. In conventional single site pacing (SSP), only one site of a particular heart chamber (e.g., the LV) is stimulated. Alternatively, multisite pacing (MSP) can be used to as an alternative to SSP. The MSP involves electrostimulation at two or more sites in a heart chamber within a cardiac cycle. For example, in LV MSP, multiple LV sites may be simultaneously stimulated, or separated by one or more intra-LV time offset (ILVD).MSP may improve LV function and hemodynamic responses in some patients. However, MSP may require more energy than SSP, and may also increase the complexity of system design and operation. Not all CHF patients can uniformly benefit more from MSP than SSP.

The stimulation timing parameters (e.g., AVD, VVD, or ILVD) define the timing and sequence of cardiac stimulation, and may have an impact on therapy efficacy and hemodynamic outcome. The stimulation timing parameters, such as AVD, may be determined using measurements of patient AV conduction, such as an interval (PRI) measured from surface electrocardiogram (ECG) between a P wave and an R wave within a cardiac cycle, or an interval (AVI) measured from an intracardiac electrogram (EGM) between an atrial sensed (AS) or atrial paced (AP) event to a ventricular sensed event (VS) within a cardiac cycle. In a patient, the PRI or AVI may not stay constant, but instead may vary under a multitude of physiological or functional conditions. For example, long-term changes in patient health conditions, HF progressions such as remodeling or decompensation, or short-term changes in heart rate, postures, posture transitions, physical activities, sleep/awake status, medication, hydration, diet, among other factors, may affect the PRI or AVI. Accordingly, the stimulation timing parameters such as AVD may also be affected by the long-term or short-term changes in patient conditions. Consequently, a HF therapy (e.g., LV-only pacing, BiV pacing, SSP, or MSP) based on a previously optimized AVD may no longer be effective or provide satisfactory patient outcome at a different patient condition. For example, a programmed AVD may be too long when patient changes posture, resulting in reduced or less optimal CRT delivery that adversely affects patient outcome.

The present inventors have recognized a number of technical challenges in electrostimulation therapy for HF. Among others, one challenge has to do with individualized HF therapy, particularly adverse impacts of changing patient conditions on therapy efficacy. In addition to inter-patient differences of responses to LV-only pacing versus BiV pacing, and responses to MSP versus SSP, there is intra-patient variations over time of responses to LV-only pacing or BiV pacing, or responses to SSP or MSP, at least because of an impact of the long-term and short-time changes in patient physiological or functional conditions. Another challenge pertains to a guarantee of adequate pacing therapy, particularly in pacing-dependent patients. For example, reduction of CRT pacing may occur in various occasions in a conventional HF management system, such as during therapy optimization. Some conventional systems may reconfigure a pacing electrode (e.g., an LV pacing electrode) to sense cardiac electrical activity. Pacing therapy may have to be suspended, albeit temporarily, so as to provide event sensing during therapy optimization process. For example, frequent reassessment of PRI or AVI when there is a changing patient condition may require reconfiguring the pacing electrode as a sensing electrode to sense ventricular activation. Suspension of pacing for frequent reassessment of PRI or AVI, even temporarily, may adversely affect patient outcome. Frequent electrode reconfiguration may also add cost in computational resources such as firmware cycle, and reduce battery life.

This document discusses, among other things, a patient management system for monitoring and treating patients with heart failure. The system may include a sensor circuit to sense cardiac signals, and a receiver to receive information about patient physiological or functional conditions such as posture and physical activities. Stimulation timing parameters under specified patient physiological or functional conditions may be determined and stored in a memory. The system may periodically reassess patient physiological or functional conditions. A therapy programmer circuit may dynamically determine, for a specific patient condition, one or more of a stimulation site, a stimulation mode, or stimulation timing using the sensor input and the stored stimulation timing parameters values. The system may include a therapy circuit to deliver or adjust an electrostimulation therapy according to the determined stimulation site, stimulation mode, and the stimulation timing.

The present document provides technical solutions to the above-identified challenges in electrostimulation therapy for HF, and therefore improves the medical technology of device-based heart failure patient management. Among other things, the present document provides approaches for providing cardiac pacing therapy (e.g., through programming therapy parameters including stimulation timing, stimulation site, and stimulation mode) tailored to individual patient and to particular patient physiological or functional condition. This document discusses an efficient approach of adjusting AVD or other stimulation timing parameters based on a stimulation parameter table that contains recommended AVD values at a multitude of patient conditions. The patient condition-indicated adjustment of stimulation timing, along with the dynamic switching between LV-only pacing and BiV pacing and dynamic switching between SSP and MSP pacing mode, may ensure consistent and effective pacing therapy to meet individual patient need under different physiological or functional conditions. In an example, this document provides a beat-to-beat adjustment of stimulation timing and switching of stimulation site or stimulation mode. The systems and methods discussed herein may improve therapy efficacy, patient outcome, and reduce healthcare cost associated with HF management. The present document also provides identification of the conditions that may affect stimulation timing and therapy efficacy. This may be beneficial for healthcare providers to track patient HF progression, and improve patient management.

This document also discusses a method to estimate the PRI or AVI during stimulation using an offset between an AVD corresponding to a pseudofusion beat and a PRI or AVI. Because the estimation process requires no suspension of pacing, sufficient pacing therapy can be achieved even during therapy adjustment; and the adverse effects on patient outcome can be avoided or reduced.

In addition to the improvement in the medical technology of device-based heart failure patient management under various patient conditions, the systems, devices, and methods discussed herein may also allow for more efficient device memory usage, such as by storing and updating the stimulation timing parameter that are clinically more relevant to patient long-term and short-term changing conditions. The individualized and dynamically adjusted therapy discussed in this document may not only improve therapy efficacy and patient outcome, but may also save device power and extend battery life. With individualized HF therapy tailored to specific patient conditions, fewer unnecessary interventions or hospitalizations may be scheduled, prescribed, or provided; as a result, overall cost savings may be realized.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIGS. 3A-3B illustrate examples of a stimulation parameter table including recommended values of stimulation timing at various patient physiological and physical conditions.

DETAILED DESCRIPTION

Disclosed herein are systems, devices, and methods for monitoring and treating patients with heart failure or other cardiac diseases. The system may sense cardiac signals, and receives information about patient physiological or functional conditions. A stimulation parameter table that includes recommended values of timing parameters such as AVD may be created at a multitude of patient physiological or functional conditions. The system may periodically reassess patient physiological or functional conditions. A therapy programmer circuit may dynamically switch between LV-only pacing and BiV pacing, switch between single site pacing and multi-site pacing based on the patient condition, or adjust the stimulation timing using the cardiac signal input and the stimulation parameter table. A HF therapy may be delivered in accordance with the determined stimulation site, stimulation mode, and the stimulation timing.

System and Apparatus for HF Monitoring and Therapy

Figure 1:
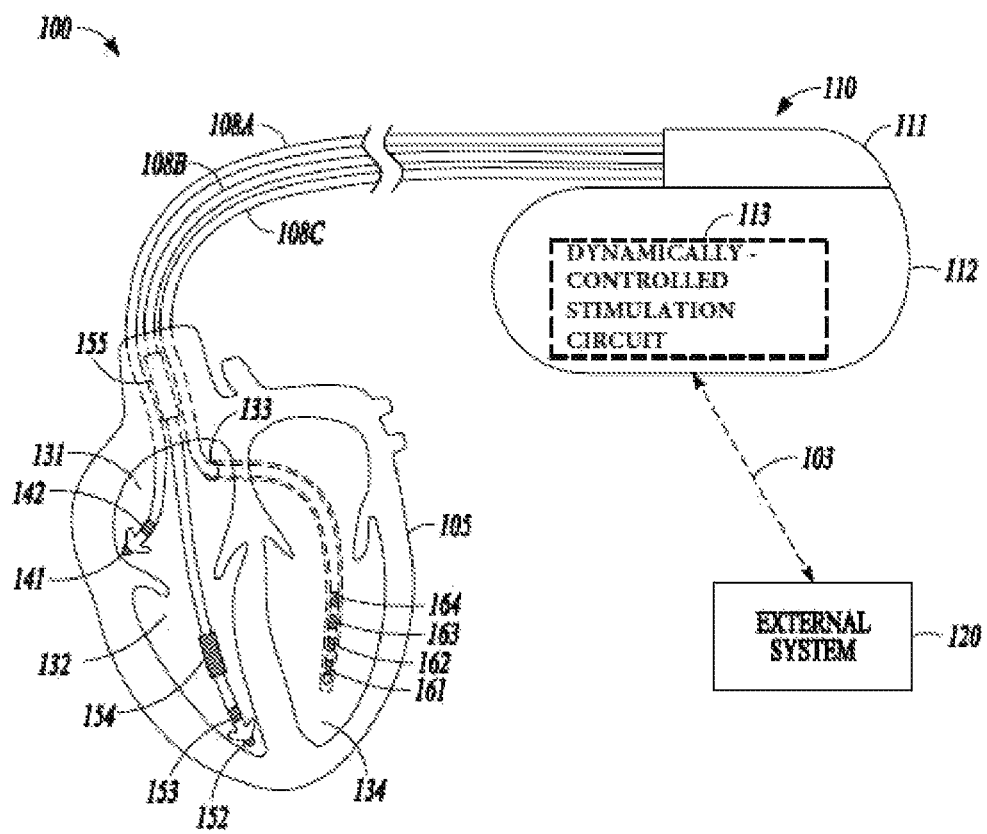
FIG. 1 illustrates an example of a patient management system and portions of an environment in which the system may operate.

FIG. 1 illustrates an example of a patient management system 100 and portions of an environment in which the patient management system 100 may operate. The patient management system 100 may include an ambulatory medical device, such as an implantable medical device (IMD) 110 that may be electrically coupled to a heart 105 through one or more leads 108A-C, and an external system 120 that may communicate with the IMD 110 via a communication link 103. Examples of the IMD 110 may include, but are not limited to, pacemakers, defibrillators, cardiac resynchronization therapy (CRT) devices, cardiac remodeling control therapy (RCT) devices, neuromodulators, drug delivery devices, biological therapy devices, diagnostic devices such as cardiac monitors or loop recorders, or patient monitors, among others. The IMD 110 may be coupled to, or may be substituted by a monitoring medical device such as a bedside or other external monitor. In addition to or in lieu of the IMD 110, other ambulatory medical device may be used, which may include subcutaneous medical device such as a subcutaneous monitor or diagnostic device, or external monitoring or therapeutic medical devices such as automatic external defibrillators (AEDs) or Holter monitors; wearable medical devices such as patch-based devices, smart watches, or smart accessories; or a bedside monitor.

The IMD 110 may include a hermetically sealed can 112 that may house an electronic circuit that may sense a physiological signal in the heart 105 and may deliver one or more therapeutic electrical pulses to a target region, such as in the heart, such as through one or more leads 108A-C. The patient management system 100 may include only one lead such as 108B, or may include two leads such as 108A-B.

The lead 108A may include a proximal end that may be connected to IMD 110 and a distal end that may be placed at a target location such as in the right atrium (RA) 131 of the heart 105. The lead 108A may have a first pacing-sensing electrode 141 that may be located at or near its distal end, and a second pacing-sensing electrode 142 that may be located at or near the electrode 141. The electrodes 141 and 142 may be electrically connected to the IMD 110 such as via separate conductors in the lead 108A, such as to allow for sensing of the right atrial activity and optional delivery of atrial pacing pulses. The lead 108B may be a defibrillation lead that may include a proximal end that may be connected to IMD 110 and a distal end that may be placed at a target location such as in the right ventricle (RV) 132 of heart 105. The lead 108B may have a first pacing-sensing electrode 152 that may be located at distal end, a second pacing-sensing electrode 153 that may be located near the electrode 152, a first defibrillation coil electrode 154 that may be located near the electrode 153, and a second defibrillation coil electrode 155 that may be located at a distance from the distal end such as for superior vena cava (SVC) placement. The electrodes 152 through 155 may be electrically connected to the IMD 110 such as via separate conductors in the lead 108B. The electrodes 152 and 153 may allow for sensing of a ventricular EGM and may optionally allow delivery of one or more ventricular pacing pulses, and electrodes 154 and 155 may allow for delivery of one or more ventricular cardioversion/defibrillation pulses. In an example, the lead 108B may include only three electrodes 152, 154 and 155. The electrodes 152 and 154 may be used for sensing or delivery of one or more ventricular pacing pulses, and the electrodes 154 and 155 may be used for delivery of one or more ventricular cardioversion or defibrillation pulses. The lead 108C may include a proximal end that may be connected to the IMD 110 and a distal end that may be placed at a target location such as in a left ventricle (LV) 134 of the heart 105. The lead 108C may be implanted through the coronary sinus 133 and may be placed in a coronary vein over the LV such as to allow for delivery of one or more pacing pulses to the LV. The lead 108C may include an electrode 161 that may be located at a distal end of the lead 108C and another electrode 162 that may be located near the electrode 161. The electrodes 161 and 162 may be electrically connected to the IMD 110 such as via separate conductors in the lead 108C such as to allow for sensing the LV EGM and optionally allow delivery of one or more resynchronization pacing pulses from the LV. Additional electrodes may be included in or along the lead 108C. In an example, as illustrated in FIG. 1, a third electrode 163 and a fourth electrode 164 may be included in the lead 108. In some examples (not shown in FIG. 1), at least one of the leads 108A-C, or an additional lead other than the leads 108A-C, may be implanted under the skin surface without being within at least one heart chamber, or at or close to heart tissue.

The IMD 110 may include circuitry that may sense a physiological signal. The physiological signal may include an EGM or a signal representing mechanical function of the heart 105. The hermetically sealed can 112 may function as an electrode such as for sensing or pulse delivery. For example, an electrode from one or more of the leads 108A-C may be used together with the can housing 112 such as for unipolar sensing of an EGM or for delivering one or more pacing pulses. A defibrillation electrode from the lead 108B may be used together with the can housing 112 such as for delivering one or more cardioversion/defibrillation pulses. In an example, the IMD 110 may sense impedance such as between electrodes located on one or more of the leads 108A-C or the can housing 112. The IMD 110 may be configured to inject current between a pair of electrodes, sense the resultant voltage between the same or different pair of electrodes, and determine impedance using Ohm's Law. The impedance may be sensed in a bipolar configuration in which the same pair of electrodes may be used for injecting current and sensing voltage, a tripolar configuration in which the pair of electrodes for current injection and the pair of electrodes for voltage sensing may share a common electrode, or tetrapolar configuration in which the electrodes used for current injection may be distinct from the electrodes used for voltage sensing. In an example, the IMD 110 may be configured to inject current between an electrode on the RV lead 108B and the can housing 112, and to sense the resultant voltage between the same electrodes or between a different electrode on the RV lead 108B and the can housing 112. A physiological signal may be sensed from one or more physiological sensors that may be integrated within the IMD 110. The IMD 110 may also be configured to sense a physiological signal from one or more external physiological sensors or one or more external electrodes that may be coupled to the IMD 110. Examples of the physiological signal may include one or more of ECG, intracardiac EGM, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, physical activity or exertion level, physiological response to activity, posture, respiration, body weight, or body temperature, among others.

In certain examples, the system 100 may include one or more leadless sensors not being tethered to the IMD 110 via the leads 108A-C. The leadless ambulatory sensors may be configured to sense a physiological signal and wirelessly communicate with the IMD 110. In some examples, the IMD 110 may be a leadless medical device. Unlike a tethered device such as the IMD 110 as illustrated in FIG. 1, a leadless medical device requires no lead, wire, or tether extended between the electrodes and the device body. The leadless medical device may include an anchoring or fixation mechanism for positioning the device body on a target implant side, such as an endocardial surface of one of a left ventricle, a right ventricle, a left atrium, or a right atrium, or an epicardial surface of a portion of the heart. The leadless medical device may be delivered transvenously and positioned within a blood vessel on the heart, such as a coronary vein, where one or more electrodes on the leadless medical device may be directly or indirectly in contact with the epicardial surface of the heart. An example of such an leadless medical device may include the leadless cardiac pacemaker (LCP) disclosed in the commonly assigned U.S. Patent Application Publication US2016/0051823 by Maile et al., entitled "LEADLESS CARDIAC PACEMAKER HAVING A SENSOR WITH A LOWER POWER MODE," which is hereby incorporated by reference in its entirety.

The arrangement and functions of these leads and electrodes are described above by way of example and not by way of limitation. Depending on the need of the patient and the capability of the implantable device, other arrangements and uses of these leads and electrodes are possible.

The patient management system 100 may include a dynamically controlled stimulation circuit 113. The dynamically controlled stimulation circuit 113 may determine therapy parameters dynamically according to patient present physiological or functional condition. Patient conditions such as patient health status, HF progressions, remodeling or decompensation, heart rate, postures, posture transitions, physical activities, sleep/awake status, medication, hydration, diet, among other factors, may affect cardiac electrical and mechanical properties, and consequently affect HF therapy efficacy. In an example, the dynamically controlled stimulation circuit 113 may determine a stimulation site such as between a LV-only pacing and a BiV pacing, or a stimulation mode such as between a SSP and MSP, based on the sensor input. The dynamically controlled stimulation circuit 113 may further determine stimulation timings such as AVD or VVD values using the sensor input and optionally a pre-determined stimulation parameter table. The stimulation parameter table contains timing values (e.g., AVD values) under various patient physical and physiological conditions. The dynamically controlled stimulation circuit 113 may deliver electrostimulation to the heart in accordance with the determined stimulation site, stimulation mode, and the stimulation timing parameters. Examples of the dynamically controlled stimulation circuit 113 are described below, such as with reference to FIG. 2.

The external system 120 may allow for programming of the IMD 110, and receiving information from the IMD 110, via a communication link 103. The external system 120 may include a local external IMD programmer. The external system 120 may include a remote patient management system that may monitor patient status or adjust one or more therapies such as from a remote location. The remote patient management system may evaluate collected patient data and provide alert notifications, among other possible functions. In an example, the remote patient management system may include a centralized server acting as a central hub for collected patient data storage and analysis. The server may be configured as a uni-, multi- or distributed computing and processing system. The remote patient management system may additionally or alternatively include one or more locally configured clients or remote clients securely connected to the server. Examples of the clients may include personal desktops, notebook computers, mobile devices, or other computing devices. System users, such as clinicians or other qualified medical specialists, may use the clients to securely access stored patient data assembled in the database in the server.

The communication link 103 may include one or more of an inductive telemetry link, a radio-frequency telemetry link, or a telecommunication link, such as an internet connection. The communication link 103 may provide for data transmission between the IMD 110 and the external system 120. The transmitted data may include, for example, real-time physiological data acquired by the IMD 110, physiological data acquired by and stored in the IMD 110, therapy history data or data indicating IMD operational status, programming instructions to the IMD 110 such as to configure the IMD 110 to perform one or more actions including, for example, data acquisition, device self-diagnostic test, or therapy delivery.

The dynamically controlled stimulation circuit 113 may be implemented at the external system 120 such as using data extracted from the IMD 110 or data stored in a memory within the external system 120. Portions of the dynamically controlled stimulation circuit 113 may be distributed between the IMD 110 and the external system 120.

Portions of the IMD 110 or the external system 120 may be implemented using hardware, software, or any combination of hardware and software. Portions of the IMD 110 or the external system 120 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals. While described with reference to the IMD 110, the patient management system 100 could include a subcutaneous medical device (e.g., subcutaneous ICD, subcutaneous diagnostic device), wearable medical devices (e.g., patch based sensing device), or other external medical devices.

Figure 2:
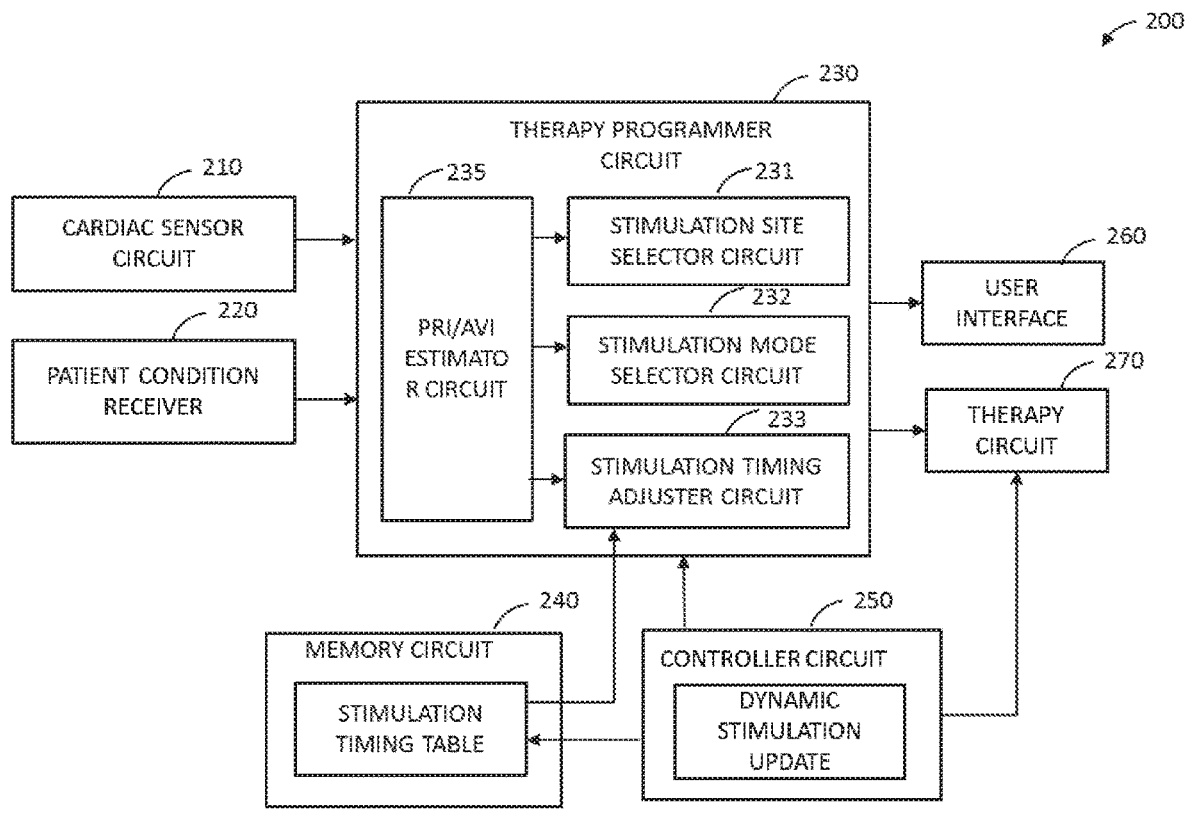
FIG. 2 illustrates an example of a dynamically controlled cardiac stimulation system configured to program and deliver electrostimulation to treat HF or other cardiac diseases.

FIG. 2 illustrates an example of a dynamically controlled cardiac stimulation system 200. The dynamically controlled cardiac stimulation system 200 may be configured to provide diagnostic information including, for example, changes of cardiac status at various patient physiological or functional conditions, and recommend therapy parameters values such as timing, site, and mode of cardiac electrostimulation. The dynamically controlled cardiac stimulation system 200 may include one or more of a cardiac sensor circuit 210, a patient condition receiver 220, a therapy programmer circuit 230, a memory circuit 240, a controller circuit 250, and a user interface 260. In some examples, the dynamically controlled cardiac stimulation system 200 may additionally include a therapy circuit 270 that may deliver or adjust a therapy such as cardiac electrostimulation. At least a portion of the cardiac monitoring system 200 may be implemented in an AMD, such as the IMD 110, or distributed between an AMD or and an external system such as the external system 120.

The cardiac sensor circuit 210 may include a sense amplifier to sense a cardiac signal. The cardiac signal may be sensed from different heart chambers, such as one or more of the RA, the RV, the left atrium (LA), or the LV. The cardiac signal may be sensed when the heart undergoes an intrinsic rhythm such as a sinus rhythm, or when the heart is stimulated in accordance with a stimulation protocol, such as pacing at an atrium, a ventricle, or other sites at a specified rate or timing sequence. Examples of the cardiac signal may include cardiac electrical signals such as ECGs sensed non-invasively from body surface, subcutaneous ECGs sensed from subcutaneously placed electrodes, or intracardiac EGMs sensed from electrodes on one or more of the leads 108A-C or the can housing 112. By way of example and not limitation, atrial activation (denoted by AS) may be sensed using a sensing vector comprising one of the atrial electrodes 141 or 142, right ventricular activation (denoted by RVS) may be sensed using a sensing vector comprising one of the RV electrodes 152-154, and left ventricular activation (denoted by LVS) may be sensed using a sensing vector comprising one of the LV electrodes 161-164.

Additionally or alternatively, the cardiac signals may include signals indicative of cardiac mechanical activities or patient hemodynamic status. In an example, the cardiac signal may include a signal sensed from an accelerometer or a microphone configured to sense heart sounds in a patient. In an example, the cardiac signal may include a cardiac or thoracic impedance signal. The cardiac mechanical signals may include blood pressure sensor signals or any other sensor signals indicative of cardiac mechanical activities or hemodynamic status.

In some examples, the cardiac sensor circuit 210 may simultaneously or sequentially sense two or more cardiac signals from different sites of a heart chamber, such as multiple sites at the LV. The cardiac sensor circuit 210 may sense LV EGMs from two or more LV sites using respective sensing vectors. An example of the LV sensing vector may include a bipolar sensing vector, such as between a pair of electrodes selected among 161-164. Alternatively, the LV sensing vector may be between one of the electrodes 161-164 and another electrode positioned on a different chamber or on a different lead (such as one of electrodes 152-155 on the RV lead 108B, or electrodes 141 or 142 on the RA lead 108A). Another example of the LV sensing vector may include a unipolar sensing vector such as between one of the electrodes 161-164 and the can housing 112.

The cardiac sensor circuit 210 may process the sensed cardiac signal, including amplification, digitization, filtering, or other signal conditioning operations. From the processed cardiac signal, the cardiac sensor circuit 210 may detect signal features, or perform measurements that indicate patient cardiac condition or therapy efficacy, or a complication introduced by the stimulation. Examples of the signal features may include temporal or morphological features indicative of intrinsic cardiac activity such as a P wave, Q wave, R wave, QRS complex, or T wave that may be detected from a surface ECG, a subcutaneous ECG, or an intracardiac EGM, timing and intensity of evoked cardiac activity such as evoked electrical or mechanical activation in response to an electrostimulation of the heart. Examples of the intensity measurement may include signal amplitude, slope or rate of change of signal amplitude, amplitude of a transformed physiological signal such as integrated signal, or a frequency-domain measurement such as power spectral density. Examples of the timing measurement may include a time delay between cardiac activations sensed at different heart chambers (e.g., PRI or AVI between an atrium and a ventricle, or RV to LV sensed interval), or between different pacing sites (e.g., sensing delay among various LV sites).

The patient condition receiver 220 may receive information about patient long-term and short-term physiological or functional conditions. Changes in long-term or short-term patient conditions may affect cardiac electrical and mechanical properties and patient hemodynamic responses. As a result, a therapy may be less effective if not timely and properly adjusted to accommodate the changing patient condition. Physiological signals, such as cardiac, pulmonary, neural, or biochemical signals, may be received at the patient condition receiver 220. Examples of the physiological signals may include ECG, intracardiac EGM, a heart rate signal, a heart rate variability signal, a cardiovascular pressure signal, a heart sounds signal, a respiratory signal, a thoracic impedance signal, a respiratory sounds signal, or blood chemistry measurements or expression levels of one or more biomarkers. Examples of the functional signals may include patient posture, gait, balance, or physical activity signals, among others. The sensor circuit may sense the functional signals using a motion sensor, such as an accelerometer, gyroscope (which may be a one-, two-, or three-axis gyroscope), magnetometer (e.g., a compass), inclinometers, goniometers, altimeters, electromagnetic tracking system (ETS), or a global positioning system (GPS) sensor, among others. In another example, the functional signal may include information about sleep state signal, such as sleep or awake state, frequency or duration of sleep position switch, sleep incline, or other indicators of sleep quality. In another example, the functional signal may include information on food or drink intake (e.g., swallow), coughing or aspiration detection. In some examples, information about patient physiological or functional conditions may be stored in a storage device, such as an electronic medical record (EMR) system, and the patient condition receiver 220 may be configured to receive the patient condition from the storage device in response to a user input or triggered by a specific event.

In some examples, the patient condition receiver 220 may receive information about patient medical history, medication intake, hospitalization, surgical procedures, cardiac remodeling, worsening heart failure events such as heart failure decompensation, or HF comorbidities. In some examples, the patient condition receiver 220 may receive device implant information, such as position of an implantable lead. For example, an LV lead 108C may be implanted at free wall, anterior, lateral, or posterior, among other possible LV positions. LV lead location may affect the therapy efficacy, and be used for determining the stimulation site, mode, and timing parameter. In some examples, the patient condition receiver 220 may additionally include patient echocardiography-derived measurements, such as ejection fraction, cardiac contractility, cardiac timing, or aortic velocity, among other hemodynamic parameters or other clinical diagnostics.

The therapy programmer circuit 230 may generate diagnostics about changes of cardiac status at a particular patient physiological or functional condition as received from the patient condition receiver 220, and recommend therapy parameter values including, for example, timing, site, and mode of cardiac electrostimulation. The therapy programmer circuit 230 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general-purpose processor that may receive and execute a set of instructions of performing the functions, methods, or techniques described herein.

The therapy programmer circuit 230 may include circuit sets comprising one or more other circuits or sub-circuits, including one or more of a PRI/AVI estimator circuit 235, a stimulation site selector circuit 231, a stimulation mode selector 232, and a stimulation timing adjuster circuit 233. These circuits may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The stimulation site selector circuit 231 may be configured to determine a heart chamber for pacing according to the received patient condition. In an example, the stimulation site selector circuit 231 may select between an LV-only pacing and a BiV pacing. The BiV pacing refers to stimulation of both the LV and RV simultaneously or sequentially with a specified time offset. In some patients, the BiV pacing may offer better cardiac synchrony and cardiac contractility than the LV-only pacing configured for only stimulating the LV. However, a change in patient physiological or functional condition (e.g., a heart rate increase, or a posture transition from supine to standing) may alter AV condition, ventricular contractility, or other cardiac properties. Pacing chamber may need to be switched, among other therapy adjustments, to maintain adequate therapy efficacy. The stimulation site selector circuit 231 may initiate stimulation site assessment in response to a change of patient condition, and determine between an LV-only pacing and BiV pacing based on a heart rate increase, and an indicator of AV conduction abnormality, such as an extension of PRI or AVI or increased irregularity of the PRI or AVI. Examples of determining stimulation site between LV-only pacing and BiV pacing to accommodate changes in patient conditions are discussed below, such as with reference to FIG. 6.

The stimulation mode selector circuit 232 may be configured to determine between a single site pacing (SSP) and a multisite pacing (MSP) according to the received patient condition. The MSP may be delivered at two or more sites inside, or on an epicardial surface of, one or more heart chambers or tissues surrounding any of the chambers. During MSP, pulse trains may be delivered at the two or more cardiac sites simultaneously, or sequentially with an intra-ventricular delay less than a sensed or paced time interval value of the cardiac cycle.

In an example, the stimulation mode selector circuit 232 may initiate stimulation mode assessment in response to a change of patient condition, and determine between SSP pacing and a MSP pacing at two or more LV sites using inter-ventricular intervals measured from RV site to various candidate LV sites, such as those corresponding to the LV electrodes 161-164. The inter-ventricular intervals represent degrees of dyssynchrony between RV and various LV sites. The stimulation mode selector circuit 232 may scan through a plurality of candidate LV electrodes to identify those LV sites with the corresponding inter-ventricular intervals satisfying a specified condition, such as a patient condition-indicated threshold value, and select SSP or MSP based on the candidate electrodes identification. Examples of determining stimulation mode between SSP and MSP to accommodate changes in patient conditions are discussed below, such as with reference to FIG. 7.

The stimulation timing adjuster circuit 233 may be configured to determine a stimulation timing parameter (e.g., AVD, VVD, or ILVD) according to the received patient condition. The stimulation timing parameters define the timing sequence of cardiac activation, and may affect therapy efficacy and patient hemodynamic response. In an example, the stimulation timing adjuster circuit 233 may determine AVD using PRI or AVI under the received patient condition. As previously discussed, the PRI or AVI may vary under a multitude patient physiological or functional conditions. PRI or AVI may be measured directly from the sensed cardiac signal under a specific patient condition. Alternatively, the PRI or AVI may be estimated dynamically during pacing, such as provided by the PRI/AVI estimator circuit 235.

The AVD may be determined as a linear combination of an interval between atrial sensed (AS) or atrial paced (AP) activation to a sensed RV activation (RVS), and an interval between AS or AP to a sensed LV activation (LVS). Alternatively, AVD values under various patient conditions may be dynamically created and stored in the memory circuit 240. Graphically, the AVD values may be organized in a stimulation parameter table, such as that depicted in FIGS.

3A-3B below. The stimulation timing adjuster circuit 233, coupled to the memory circuit 240, may search for the received patient condition from the stimulation parameter table, and identify a recommended AVD corresponding to that patient condition. The stimulation timing adjuster circuit 233 may perform dynamic AVD adjustment by switching to the applicable table entry whenever the patient is in that condition. In an example, the AVD may be adjusted on a beat-by-beat basis. Examples of adjusting AVD using a patient condition-indicated stimulation parameter table are discussed below, such as with reference to FIGS. 3-4.

The PRI/AVI estimator circuit 235 may be configured to dynamically determine PRI or AVI during pacing. The PRI/AVI estimator circuit 235 may be coupled to one or more of the stimulation site selector circuit 231, the stimulation mode selector circuit 232, or the stimulation timing adjuster circuit 233. The circuits 231-233 may use the dynamically determined PRI or AVI to update the stimulation parameter table, or to determine between LV-only pacing and BiV pacing, or to determine between SSP and MSP.

The PRI/AVI estimator circuit 235 may be configured to measure an offset between an AVD corresponding to a pseudofusion beat and a PRI or AVI, such as through a testing process, as to be discussed in the following with reference to FIG. 5. The offset may be stored for future use. When a change patient physiological or functional condition is detected, the PRI or AVI may be estimated using a combination of the AVD that leads to pseudofusion and the stored offset. As such, the PRI or AVI may be estimated without suspension of ventricular pacing. Examples of dynamic determination of PRI or AVI during pacing are discussed below, such as with reference to FIG. 5.

The therapy circuit 270 may be configured to generate therapy according to the parameter values generated and recommended by the therapy programmer circuit 230. The therapy may include electrostimulation delivered to the pacing sites via one or more of the leads 108A-C and the respectively attached electrodes. The therapy circuit 270 may be configured to deliver LV-only pacing, or BiV pacing. Additionally or alternatively, the therapy circuit 270 may be configured to generate SSP for stimulating one cardiac site, or a MSP for stimulating two or more sites of the heart within the same cardiac cycle. In an example, the MSP may be delivered within the LV. The LV MSP may have a unipolar pacing configuration where only one electrode (e.g., the cathode) is a LV electrode and the other electrode (e.g., the anode) is the IMD can housing 112. In another example, a true bipolar configuration may be used, where both the cathode and anode are LV electrodes. In yet another example, an extended bipolar configuration may be used, where one electrode (e.g., the cathode) is a LV electrode and the other electrode (e.g., the anode) is a RA electrode such as one of the electrodes 141 or 142, or a RV electrode such as one of the electrodes 152-155. In another example, a tripolar configuration may be used, which may involve two LV electrodes used jointly as the cathode, or two electrodes such as selected from the RA and RV electrodes used jointly as the anode. In some examples, one or more LV electrodes may be distributed in one or more LV leads, catheters, or untethered pacing units.

In some examples, the therapy circuit 270 may initiate or adjust electrostimulation at non-cardiac tissues such as nerve tissues, or other therapy types, such as a cardioversion therapy, a defibrillation therapy, or drug therapy including delivering drug to a tissue or organ. In some examples, the therapy circuit 270 may modify an existing therapy, such as adjust a stimulation parameter or drug dosage.

The controller circuit 250 may control the operations of the therapy programmer circuit 230, the memory circuit 240, the therapy circuit 270, and the data flow and instructions between these components and respective subcomponents. In an example, the controller circuit 250 may update the stimulation parameter table. The stimulation parameter table may be updated periodically, or in response to a trigger event. In some examples, the controller circuit 250 may update the stimulation parameter table at a frequency according to table update history, such as a trend of table update, such that next update may be scheduled according to the historical trend. Examples of creating and updating the stimulation parameter table are discussed below, such as with reference to FIG. 4. The controller circuit 250 may additionally control the therapy circuit 270 to deliver HF therapy according to the selected stimulation site, stimulation mode, and the stimulation timing parameters.

The user interface 260 may include an input device that enables a system user to program the parameters used for electrostimulation or for sensing the cardiac signals. Examples of the input device may include a keyboard, on-screen keyboard, mouse, trackball, touchpad, touchscreen, or other pointing or navigating devices. The input device may enable the system user to activate automated programming of HF therapy, such as automated determination of stimulation site, stimulation mode, and stimulation timing parameters under a specific patient condition. The input device may also enable the system user to confirm, reject, or otherwise modify the automatically determined therapy programming.

The user interface 260 may include a display for display therapy programming such as automatically determined stimulation site, stimulation mode, and stimulation timing parameters. The output unit 230 may include a printing device for producing a hardcopy of the information. The information may be presented in a table, a chart, a trend, a diagram, or any other types of textual, tabular, or graphical presentation formats. Additional information for displaying may include cardiac signals sensed from the cardiac sensor circuit 210, signal features or measurements (e.g., PRI or AVI) derived from the sensed cardiac signal, information of patient physiological or functional conditions received from the patient condition receiver 220, or device status information such as lead impedance and integrity, battery status such as remaining lifetime of the battery, or cardiac stimulation threshold, or complications associated with stimulation at one or more cardiac sites, among others.

Patient Condition-Indicated Pacing Optimization

FIGS. 3A-3B illustrate examples of a stimulation parameter table that includes recommended values of stimulation timing at various patient physiological and physical conditions. Examples of the conditions may include posture (e.g., supine, sitting, standing, among other postures, or transitions between postures), walking, running, sleeping, time of day (e.g., daytime, nighttime, or a particular duration during the day), diet, hydration, medication intake, heart rate, heart rate variability, arrhythmic events (e.g., atrial fibrillation, ventricular tachycardia, premature ventricular contractions, post arrhythmia), atrial activation mode (e.g., atrial pace or atrial sense), among others. The present inventors have recognized that said conditions, individually or in combination, may affect cardiac tissue properties and patient hemodynamics. As a result, a therapy programmed under one condition may not be equally effective under a different condition. Different AVD values may be recommended at different patient conditions to achieve desirable therapy efficacy and patient outcome.

Table 300 shown in FIG. 3A and table 350 shown in FIG. 3B may each be implemented as a multi-dimensional array, an association map, or other data structures for storing in the memory circuit 240. By way of example and not limitation, the table 300 includes stimulation timing values, such as AVD values, at specific heart rate (HR) 310, posture 320, and atrial activation mode 330. The HR 310 may be categorized into a plurality of HR ranges, the posture 320 may include one or more of a supine, a sitting, or a standing posture, and the atrial activation mode 330 may include one or more of atrial sense (AS) and atrial pace (AP) modes. The AVD for AS is hereinafter referred to sensed AVD, and the AVD for AP is hereinafter referred to paced AVD. Each entry of the table 300 may include a recommended AVD value under a corresponding patient condition. For example, table entry 301 contains a recommended paced AVD, denoted by AVD*, corresponding to a heart rate falling within 60-70 bpm range and a standing posture. When the AVD* is programmed to the therapy circuit, a ventricular pacing pulse may be delivered following an atrial pace at an offset of AVD* if no intrinsic ventricular activity is detected within the period of AVD*. In some examples, the table 300 may include stimulation timing values (e.g., AVD values) at specific heart rate (HR) 310 and atrial activation mode 330 regardless of patient posture. In other words, the posture 320 may be excluded from the table 300. Table 350 shown in FIG. 3B includes stimulation timing values, such as AVD values, at specific HR 310, time of a day 340, and the atrial activation mode 330. By way of non-limiting example and as illustrated in FIG. 3B, the time of a day 340 may include daytime and nighttime. Each entry of the table 350 may include a recommended AVD value under a corresponding patient condition. For example, table entry 302 contains a recommended paced AVD, denoted by AVD*, corresponding to a heart rate falling within 60-70 bpm range during a nighttime. In an example, the time of a day 340 may include a number of time periods during a day within a 24-hour period. In various examples, the table 300 or 350 may be augmented to include other conditions. For example, the table 300 may include time of a day 340, or the table 350 may include information about patient posture 320. Various combination or permutations of patient conditions, including but not limited to the HR 310, posture 320, atrial activation mode 330, and time of a day 340, have been contemplated by the present inventors to be implemented in a stimulation parameter table similar to the table 300 or 350, which is within the scope of the present document.

In various examples, at least some entries of the table 300 or 350 may additionally or alternatively include recommended values of stimulation timing parameters other than AVD. In an example, the table entry may include a recommended RV-LV delay (VVD) under corresponding patient conditions of heart rate, posture, and atrial activation mode. The VVD represents an offset between an LV pacing pulse and a RV pacing pulse within a cardiac cycle for BiV pacing or CRT therapy such as selected by a system user or determined by the stimulation site selector circuit 231. In some examples, the VVD can be set to zero such that LV pacing and RV pacing are simultaneously delivered. In another example, at least some table entries may include a recommended intra-LV time offset (ILVD). The ILVD represents an offset between LV pacing pulses separately delivered at different LV sites within a cardiac cycle when a LV MSP is selected by a system user or determined by the stimulation mode selector circuit 232. The LV MSP may be delivered via two or more of the LV electrodes 161-164 as illustrated in FIG. 1.

The table 300 or 350 may be augmented to include information in addition to the stimulating timing parameters. In an example, at least some entries of the table 300 or 350 may additionally or alternatively include information about stimulation site such as an indication of LV-only pacing or a BiV pacing, or information about stimulation mode such as an indication of SSP or MSP. As discussed above with reference to FIG. 2, a selection between LV-only pacing or a BiV pacing, or a selection between SSP or MSP, may vary at different patient physical and physiological conditions. The augmented table 300 or 350 thus provides comprehensive therapy recommendations on stimulation site, mode, and timing values at various patient conditions. In an example, the entries of the augmented table 300 or 350 may be constructed as a class structure in the memory circuit 240 that contains values of one or more of the stimulation site, mode, and timing parameters. For example, one table entry may include (AVD, LV-only pacing), and another table entry may include (AVD, BiV pacing, VVD, MSP, ILVD). In an example, one element in a table entry (e.g., AVD value, BiV pacing, or MSP) may be applied to a number of table entries that share a common condition. For example, if BiV pacing is recommended for a condition defined by sitting posture, AS, and HR great than 100 bpm, then BiV pacing may be recommended for all conditions as long as containing a "sitting" posture, regardless of heart rate ranges, or atrial activation mode (AS or AP). In another example, if MSP is recommended for a condition defined by standing posture, AS, and HR within 70-80 bpm, then MSP may be recommended for all conditions as long as containing a "standing" posture, regardless of heart rate ranges, or atrial activation mode.

In some examples, multiple tables of stimulation timing parameter values may be constructed and stored in the memory circuit 240, such as an AVD table containing only AVD values under various patient conditions, a VVD table containing only VVD values under various patient conditions, or an ILVD table containing only ILVD values under various patient conditions. The tables may include different patient physiological or functional conditions. In an example, the stimulation timing adjuster circuit 233 may refer to the VVD table to determine an optimal VVD value under a specific patient condition when a BiV pacing is selected, such as via the stimulation site selector circuit 231. In another example, the stimulation timing adjuster circuit 233 may refer to the ILVD table to determine an optimal ILVD value under a specific patient condition when MSP mode is selected, such as via the stimulation mode selector circuit 232. The stimulation timing adjuster circuit 233 may refer to AVD table irrespective of the selection of stimulation site and the selection of stimulation mode.

Figures 4A, 4B:
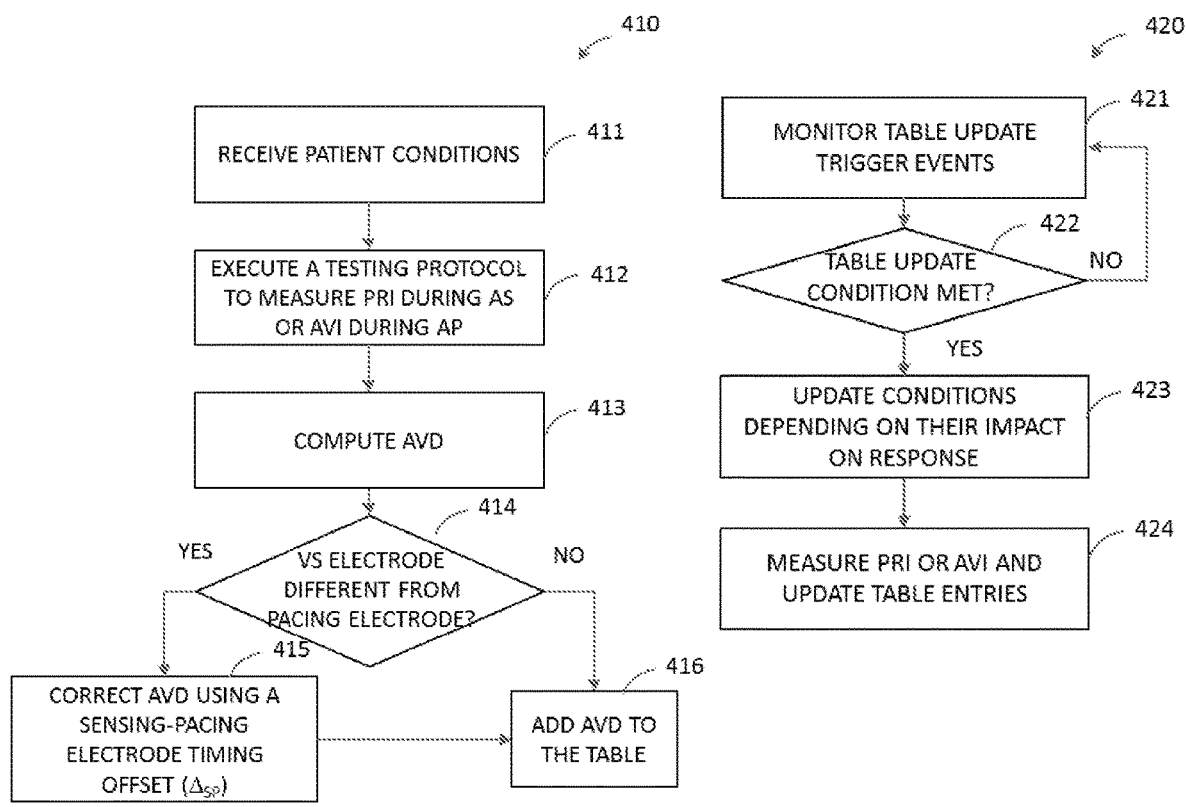
FIGS. 4A-B illustrate examples of methods for initializing and updating a stimulation parameter table.

FIGS. 4A-B illustrate methods for initializing and updating a stimulation parameter table, such as the table 300 or 350. The table initialization and update methods may be implemented in and executed by the controller circuit 250 as illustrated in FIG. 2. As illustrated in the flow chart 410 in FIG. 4A, table initialization begins at 411, where patient physiological and physical conditions to be included in the table are received. An impact of the patient condition on cardiac responses and patient hemodynamics may be analyzed. In an example, the impact of patient condition may be assessed using a change in P wave to R wave interval (PRI) (such as measured from a ECG or an intracardiac EGM), thoracic impedance, heart sounds, or pulse transit times under a specified patient physiological or functional condition from their respective baseline measurements. Patient conditions having an impact on patient hemodynamic responses or cardiac responses may be included in the stimulation parameter table.

At 412, a testing protocol may be executed. The testing protocol may include establishing various patient conditions, such as having the patient to maintain a specific posture, inducing patient heart rate (e.g., through atrial pacing or through controlled exercise) to a specified heart rate range, or establishing other patient conditions. The PRI during atrial sense AS, or the AVI during atrial pace AP, may be measured. The measurement of PRI or AVI may include sensing ventricular response at one or more of an RV sensing (RVS) site or an LV sensing (LVS) site, such as using an RV sensing vector comprising an RV electrode (e.g., one of 152-154), or an LV sensing vector comprising an LV electrode (e.g., one of 161-164). The RV or LV sensing vector may be a unipolar sensing vector comprising an RV or LV sensing electrode as a cathode and the device can 112 as an anode. In an example, the PRI or AVI measured at 412 may include one of more of AS to RVS interval, AS to LVS interval, AP to RVS interval, and AP to LVS interval. In some examples, the testing protocol may include acquiring additional information such as patient echocardiography-derived measurements, or other hemodynamic parameters or clinical diagnostics under various patient conditions.

At 413, one or more stimulation timing parameters, such as AVD, may be computed using the PRI or AVI measurements or optionally along with other information acquired at 412. Sensed AVD and paced AVD may each be computed using a combination of the PRI or AVI measured at the RV and LV. In an example, the AVD is determined using a weighted combination, such as in the following equation:

$$AVD = k1*AV_R + k2*AV_L + k3 \qquad (1)$$

In Equation (1), the $AV_R$ denotes the interval between AS or AP to RVS, and the $AV_L$ denotes the interval between AS or AP to LVS. In an example, if the inter-ventricular interval between RV and LV, $\Delta_{LR} = AV_L - AV_R$, is less than zero, then AVD may be computed using only the $AV_L$, that is, $AVD = k2*AV_L$. In an example, k2 is approximately between 0.5 and 1. If $\Delta_{LR}$ is equal to or greater than zero, then AVD may be computed as a weighted combination of $AV_R$ and $AV_L$, as given in Equation (1) above. The weight factors k1 and k2, and the scalar bias k3, may be chosen according to synchrony of the LV and RV sensing. In an example, the weight factors may be empirically determined using pacing data from patient population, data obtained from echocardiography study, or other clinical diagnostics. In an example, weight factors may respectively generated and used to compute AVD for different ventricular stimulation site (LV-only or BiV), or for different LV lead location (e.g., anterior LV or free wall).

In some examples, the AVD computation may additionally include a beat screening process. A sufficient number (e.g., 3-20) of LVS or RVS beats that satisfy a sensing criterion during AS is required to obtain a more reliable sensed AVD. Similarly, a sufficient number (e.g., 3-20) of LVS or RVS beats that satisfy a sensing criterion during AP is required to obtain a more reliable paced AVD. In an example, a median, a mean, or other central tendency over a plurality of PRI or AVI measurements is used to determine the AVD, such as according to Equation (1). In some examples, if there is no sufficient LVS or RVS beats within a specified time or a number of cardiac cycles, then the paced AVD can be determined using the sensed AVD. In an example, if $\Delta_{LR}$ is greater than zero milliseconds (msec), then the sensed AVD may be determined to be approximately 60 msec longer than the sensed AVD. If $\Delta_{LR}$ is equal to or less than zero msec, then the sensed AVD may be determined to be approximately 45 msec longer than the sensed AVD.

The AVD thus determined depends on RVS or LVS. In some examples, the RV or LV sensing electrode may be different from the RV or LV pacing electrode. Because the AVD is estimated using the measurement from the RV or LV sensing electrode, the estimated AVD may not be optimal when applied to a different RV or LV pacing electrode to deliver a pacing therapy, at least because of a time offset (ASP) between cardiac activations at the sensing electrode site and the pacing electrode site. Referring to FIG. 1, by way of example and not limitation, a sensing electrode LV1 161 is used for measuring the $AV_L$ (the interval between AS or AP to LVS), while the LV pacing is delivered via a LV pacing vector comprising a different electrode LV3 163 and the can 112. The sensing-pacing electrode time offset $\Delta_{SP}$ between the electrodes LV1 and LV3, may be measured under a known patient condition, and applied over to other patient conditions. By way of example and not limitation, the $\Delta_{SP}$ may be measured under a relatively easily manageable patient condition, such as pacing at a lower rate limit (LRL) when the patient is in a prone position. The measured $\Delta_{SP}$ may be stored in the memory circuit 240 for future use.

At 414, if it is determined that the RV or LV sensing electrode is different from the RV or LV pacing electrode, then at 415 the AVD at various patient conditions, including conditions different from the easily manageable condition under which the $\Delta_{SP}$ is determined, may be corrected by adding the sensing-pacing electrode time offset $\Delta_{SP}$. The corrected AVD may be added to the stimulation parameter table at 416. If at 414 the same ventricular electrode is used for ventricular sensing and ventricular pacing, then no AVD correction is necessary; the AVD computed at 413 may be added to the stimulation parameter table at 416. In some examples, conditions under which the AVD are computed, such as the HR range, patient posture, atrial activation mode (e.g., AS or AP), or time of a day as illustrated in FIGS. 3A-3B, may be screened against their respective interactive limits. For example, under a particular patient condition, the AVD may be determined when the pacing rate is limited by the lower rate limit (LRL) and/or the maximum tracking rate (MTR). The interactive limits may be programmed to the system or device that executes the testing protocol. Such interactive limits for the patient conditions can be beneficial for safe operation during the execution of the testing protocol in the table initialization as well as during electro-stimulation therapy according to the AVD values in the table.

FIG. 4B is a flow chart 420 illustrating a method of updating the stimulation parameter table, such as a table created using the method 410. The table may be updated periodically at specified time, such as every minute, every few minutes, every hour, every day, every a specified few days, every week, every month, etc. In some examples, the frequency of table update may be determined using table update history, such as a trend of table update. The next table update may then be scheduled according to the historical trend. For example, the next table update may be scheduled to be no longer than the shortest update period (i.e., time interval between two adjacent updates) within a timespan (e.g., a year) in patient history.

The update of the stimulation parameter table may be performed on the entire table or a portion of the table, such as those table entries corresponding to one specific condition (e.g., standing posture). The frequency of table update may vary for different portions of the table, such that one portion of the table may be updated more frequently than another portion of the table. In an example, table entries corresponding to more commonly occurred conditions, such as lower HR ranges (e.g., <100 bpm), may be updated more frequently than table entries corresponding to uncommon or less attainable conditions such as higher hear ranges (e.g., >100 bpm).

Additionally or alternatively, the table update may be triggered by a specific event. At 421, trigger events for table update are monitored, including, for example, amount (e.g., percentage) of pacing therapy patient received over a specified time period, worsening heart failure or decompensation events, hemodynamic response trend to CRT, heart rate, posture, physical activity, heart sounds, occurrence of intrinsic beats, a sudden big change in AVD recommendation, among others. In an example, table update frequency may be determined based on variability of PRI or AVI under specified patient condition. In an example, a variance, a standard deviation, a range, or other measures of spreadness may be computed from a plurality of PRI or AVI under specific patient conditions. A higher PRI variability, such as when exceeding a specified threshold, may indicate an irregular AV conduction and less efficient cardiac function under specific patient conditions. This may trigger assessment and update of the stimulation parameter table.

If at 422 one or more trigger events occur and satisfy specific conditions (e.g., exceeding a threshold value or falling within a specified value range), then at 423, patient physiological or functional conditions may be assessed to determine whether they continue to impact patient cardiac or hemodynamic responses. Depending on the impacts, an existing condition may be removed from the table, or a new condition may be integrated into the table. At 424, the PRI during AS or AVI during AP may be re-measured under the updated conditions, and the AVD, or along with other timing parameters, may be determined, such as using a similar approach as previously discussed with reference to FIG. 4A.

The update of the table entries, such as the AVD or other stimulation timing parameters, require sensing of RV or LV activities (RVS or LVS, respectively) and measuring PRI or AVI. Conventionally, this may require at least temporary suspension of ventricular pacing therapy. This may be disadvantageous because even withholding the pacing for a short period of time may cause detrimental patient outcome. To ensure uninterrupted pacing during table update, a method of dynamic PRI or AVI determination may be used, such as that discussed below with reference to FIG. 5. PRI or AVI may be estimated and the stimulation parameter table may be update without requiring a suspension of pacing therapy, or otherwise compromising the ongoing pacing therapy.

PRI/AVI Determination while Pacing

Figure 5:
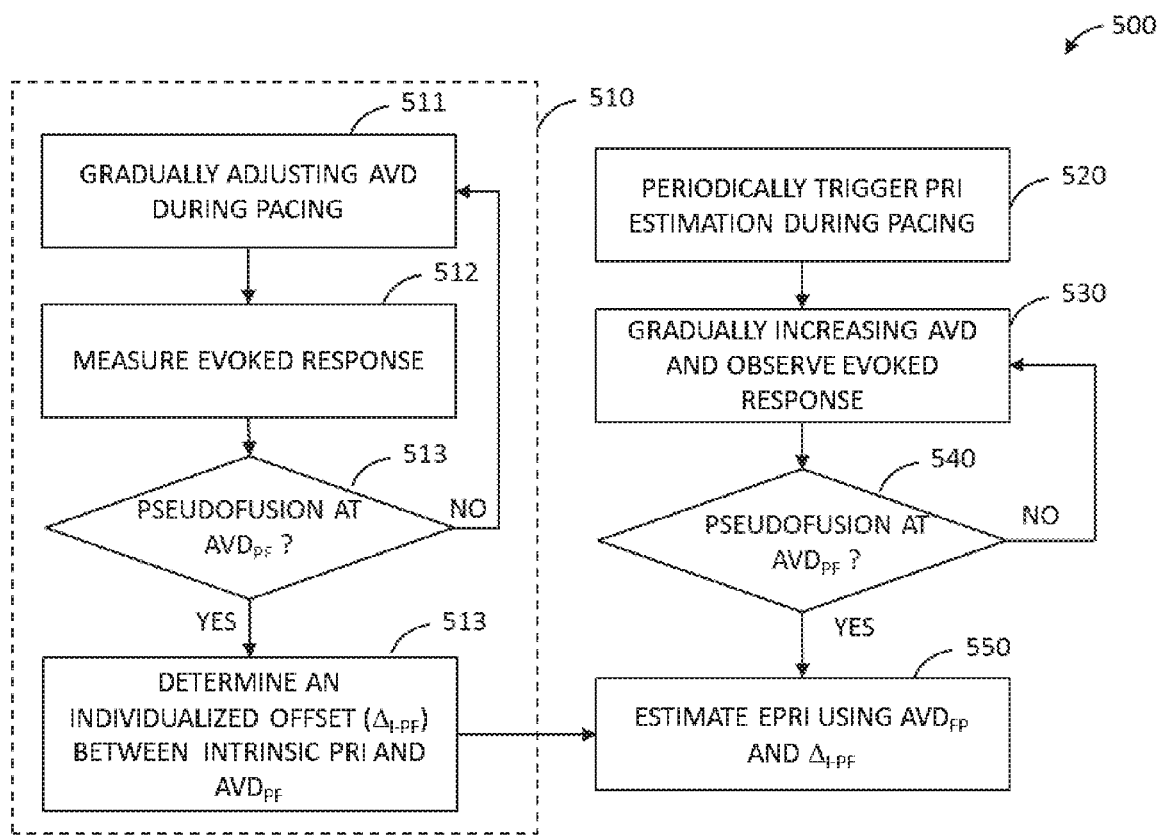
FIG. 5 illustrates an example of a method for dynamic determination of PRI or AVI during pacing.

FIG. 5 illustrates a method 500 for dynamically determining PRI or AVI during pacing. The method 500 may be implemented in and executed by the system 200. Dynamically determined PRI or AVI may be used for updating the stimulation parameter table, switching between LV-only pacing and BiV pacing, switching between SSP and MSP, or other processes requiring an estimate of PRI or AVI without suspension of ventricular pacing therapy.

The method 500 includes a process 510 for estimating an offset ($\Delta_{I\text{-}PF}$) under a controlled patient condition, such as a known heart rate range and a known posture. The offset $\Delta_{I\text{-}PF}$ may be determined between an AVD corresponding to a pseudofusion beat and a PRI or AVI. A pseudofusion beat is an electrocardiographic representation of a cardiac depolarization produced by superimposition of an ineffectual pacing stimulus on an intrinsic cardiac depolarization, such as a spontaneous QRS complex on the ECG, or an intrinsic ventricular beat on a ventricular EGM. Pseudofusion occurs when intrinsic heart rate is very close to the pacing rate. The pacing stimulus, such as a RV pacing spike or an LV pacing spike delivered according to an AVD, is ineffectual because it temporally occurs within the absolute refractory period of the spontaneous QRS.

At 511, an AVD may be gradually adjusted, and the ventricular pacing may be delivered according to the adjusted AVD. In an example, the AVD may be initialized to a small value shorter than the PRI, and gradually increase at a specified step size, such as approximately 5-10 msec. In another example, AVD may start from a large initial value greater than PRI and gradually decreases at a specified step size. Ventricular pacing may be delivered at each of the gradually adjusted AVD value. Evoked cardiac responses to ventricular pacing may be monitored from ECG, intracardiac EGM, or a physiological sensor signal. In an example, the evoked cardiac responses includes morphologies of a cardiac electrical signal sensed by an RV or LV sensing electrode. In another example, the evoked cardiac response includes morphologies of a heart sound signal or a signal indicative of cardiac mechanical response to pacing. The pseudofusion has a characteristic morphology with superimposed pacing spike on the intrinsic QRS complex or intrinsic ventricular morphology. If at 513 the morphologies indicate that pseudofusion has occurred, then from the superimposed waveform morphology, an individualized offset $\Delta_{I\text{-}PF}$ may be measured as an interval between $AVD_{PF}$ and the intrinsic PRI, that is, $\Delta_{I\text{-}PF}=PRI-AVD_{PF}$, where $AVD_{PF}$ represents the AVD that induces the pseudofusion. If no pseudofusion occurs at 513, adjustment of AVD may continue at 511. In some examples, the offset $\Delta_{I\text{-}PF}$ may be in a range between approximately 10-15 msec. The offset $\Delta_{I\text{-}PF}$ may be stored in the memory circuit 240 for future use.

A process of dynamic PRI or AVI determination may begin at 520 where a PRI estimation during pacing therapy (such as a CRT or MSP) may be periodically triggered. The events that triggers PRI estimation may include stimulation parameter table update, stimulation site update (e.g., switching between LV-only pacing and BiV pacing), or stimulation mode update (e.g., switching between SSP and MSP), among others. At 530, the AVD of the present, ongoing pacing therapy may be gradually increased, such as at a specified step size of approximately 5-10 msec. Ventricular pacing morphologies may be monitored during pacing at gradually lengthened AVD. If at 540 a pseudofusion morphology is detected, then AVD adjustment process may be terminated, and the present AVD corresponding to the pseudofusion, $AVD_{PF}'$, may be recorded. Note that the $AVD_{PF}'$ is measured under the present patient condition, which may be different from the patient condition where the $AVD_{PF}$ and $\Delta_{I\text{-}PF}$ are determined at 513. At 550, an estimated PRI, ePRI, at the present patient condition may be estimated using the $AVD_{PF}'$ and the stored offset $\Delta_{I\text{-}PF}$:

$$ePRI=AVD_{PF}'+\Delta_{I\text{-}PF} \qquad (2)$$

The estimation of the PRI according to (2) assumes the $\Delta_{I\text{-}PF}$ is not substantially affected by changing patient condition. Because the AVD extension at 530 stops at pseudofusion (at which point the pacing therapy is still delivered) and never goes beyond that point, pacing therapy can be effectively maintained during the PRI determination process. Additionally, using the pre-stored $\Delta_{I\text{-}PF}$ may also reduce time for PRI or AVI computation, save battery power, and conserve computational resources.

The estimated PRI or AVI may be used to update stimulation timing parameters, such as AVD according to Equation (1), or be used to reassess and select stimulation site between LV-only pacing and BiV pacing under various patient physiological or functional conditions, as to be discussed with reference to FIG. 6. Inter-ventricular delay between an RV sensing site and one or more LV sensing sites can be derived from the estimated PRI or AVI. The inter-ventricular interval may be used to assess stimulation mode selection between SSP and MSP under various patient conditions, as to be discussed in the following with reference to FIG. 7.

Dynamic Stimulation Site Switching Between LV-Only Pacing and BiV Pacing

Figure 6:
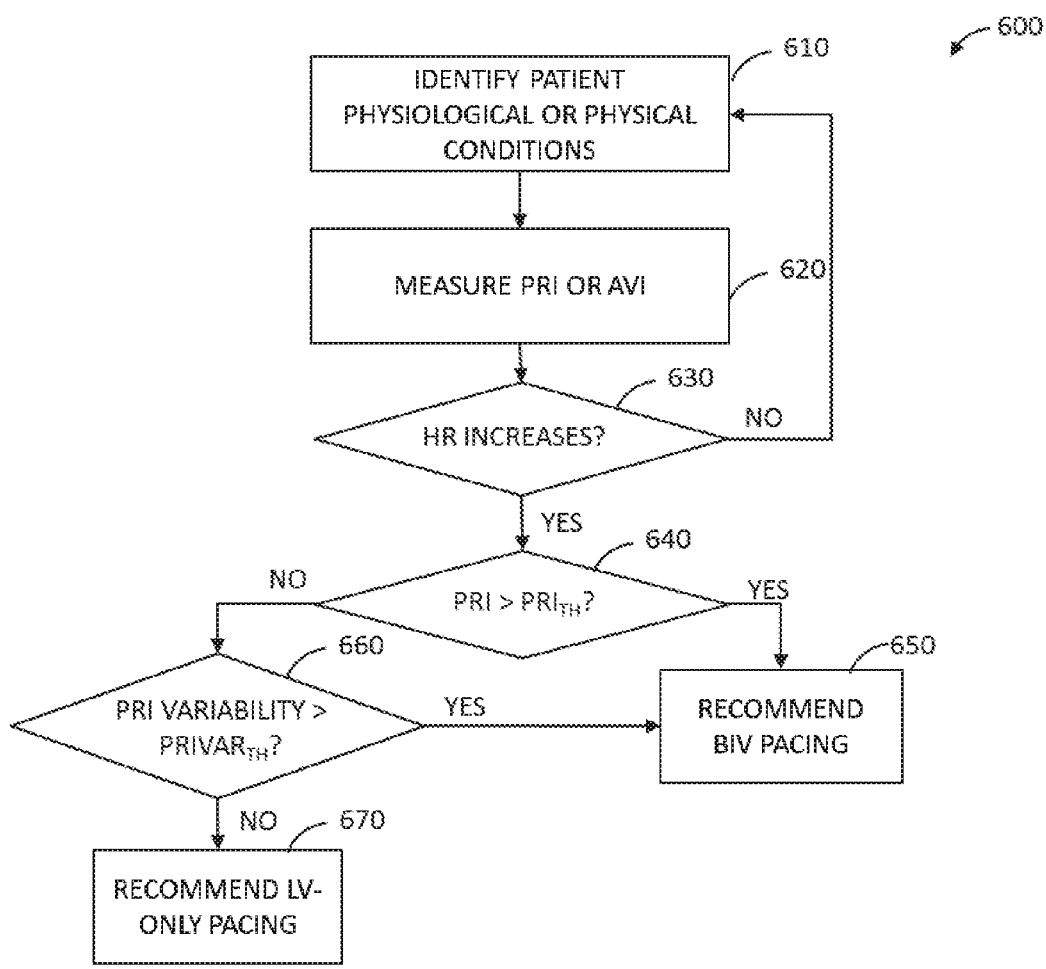
FIG. 6 illustrates an example of a method for determining between LV-only pacing and BiV pacing.

FIG. 6 illustrates an example of a method 600 for determining between LV-only pacing and BiV pacing. The method 600 may be implemented in and executed by the stimulation site selector circuit 231, as illustrated in FIG. 2. In an example, the method 600 may be used to determine stimulation site (LV-only pacing or BiV pacing) on a beat-by-beat basis, or to adjust the stimulation site periodically at specified time.

The method 600 begins at 610 where the patient physiological or functional conditions are identified. Patient conditions, such as heart rate, patient posture, physical activity, atrial activation mode, among others, may have an impact on the hemodynamic outcome during LV-only pacing or BiV pacing. At 620, PRI or AVI are measured. The PRI may be measured from surface ECG, and AVI may be measured from an atrial sense (AS) or atrial pace (AP) event to a right ventricular sense (RVS) event. In an example, the PRI or AVI may be estimated while maintaining the pacing therapy, such as using the method 500 based on pseudofusion detection. At 630, a trigger event is detected. The trigger event may include a change in patient physiological or functional condition, such as a posture change, physical activity intensity change, or a chronic change in patient HF status such as a decompensation event. In an example, the trigger event includes an increase in heart rate when the patient maintains the current physiological or physical condition. For example, if X out of Y beats exceed a heart rate threshold, then a stimulation site assessment may be triggered. In an example, three out of five consecutive beats exceeding a rate cutoff of 100 beats per minute (bpm) may trigger the stimulation site assessment. Alternatively, at 630, the stimulation site assessment may be performed periodically at a specified time.

If the heart rate criterion is satisfied at 630, the measured PRI may be compared to a PRI threshold. PRI$_{TH}$, at 640. In an example, the PRI$_{TH}$ is approximately in a range between 250-270 msec. In some examples, the threshold PRI$_{TH}$ may be determined for various patient conditions empirically, such as using echocardiography data or other heart failure diagnostics. The PRI$_{TH}$ may be patient condition dependent, such that the PRI$_{TH}$ at one patient condition may be different from the PRI$_{TH}$ at another different patient condition. In an example, the PRI$_{TH}$ may be heart rate dependent. The PRI$_{TH}$ at the device's lower rate limit (LRL) may be set to a first value, such as approximately 270 msec. The PRI$_{TH}$ at the device's maximum tracking rate (MTR) may be set to a lower value, such as approximately 200 msec. The PRI$_{TH}$ at heart rates between the LRL and MTR may be interpolated between 200 msec and 270 msec using a linear, piece-wise linear, exponential, or other nonlinear curve. If the PRI exceeds the patient condition-indicated threshold PRI$_{TH}$, then a BiV pacing is recommended at 650.

If the PRI does not exceed the threshold PRI$_{TH}$, variability of the PRI may be evaluated at 660. The variability may be measured using a variance, a standard deviation, a range, or other measures of spreadness from a plurality of PRI or AVI under the specified patient condition. If at 660 the PRI variability exceeds a patient condition-indicated PRI variability threshold PRIvar$_{TH}$ then BiV pacing is recommended at 650. A more variable PRI may indicate irregular AV conduction and cardiac function deterioration, in which case a BiV pacing may be preferred over the LV-only pacing to provide enhanced synchronous ventricular contractions and improved cardiac performance. If PRI is not substantially lengthened (e.g., falling below the threshold PRI$_{TH}$) and is less variable (e.g., falling below the variable threshold PRIvar$_{TH}$), then LV-only pacing may be recommended at 670.

Stimulation site selection, or switching between LV-only and BiV pacing, may be performed on a beat-by-beat basis. Alternatively, to improve reliability of PRI and PRI variability measurements, the PRI and PRI variability may be analyzed over a plurality of N heart beats, where N is a positive integer. In an example, N is between 10 and 20 beats. The N beats may be consecutive beats. Alternatively, the N beats may be non-consecutive. For example, a heart beat is sensed every 5-15 seconds and the PRI is computed from that heart beat, and N PRIs may be computed from the N beats. The decisions at 640 and 660 may be based on at least M out of N heart beats show an extension of PRI (at 640) or increased variability (at 650). In an example, M is equal to or great than 50% of N. In another example, the LV-only or BiV pacing decisions may be evaluated over a plurality of N beats. If LV-only pacing is recommended for all N beats, then LV is recommend at 670. If BiV pacing is recommended for all N beats, or a mixture of LV-only pacing and BiV-pacing across the N beats, then BiV pacing is recommended at 650.

The method 600 determines between LV-only pacing and BiV pacing based on AV conduction property, including an extension or increased variability of PRI or AVI. The method 600 may additionally using sensed inter-ventricular interval to determine the stimulation site. The inter-ventricular interval represents the activation delay between LV and RV, and may be computed as a difference between (1) the AS to RVS interval and (2) the AS to LVS interval, or a difference between (1) the AP to RVS interval and (2) the AP to LVS interval. In an example, if the inter-ventricular interval is less than a threshold (e.g., 20 msec), which may indicate an absence of left bundle branch block, then BiV pacing is recommended at 650. If the inter-ventricular interval is equal to or greater than the threshold (indicating RV activation substantially lags behind LV activation, such as exceeding 20 msec), then the PRI and PRI variability criteria at 640 and 660 may be applied to determine between the LV-only pacing and the BiV pacing.

In some examples, information about LV lead position may be included in the method 600 to determine the stimulation site. The lead position may be provided by a user or received through the patient condition receiver 220. In an example, even if the PRI and PRI variability criteria at 640 and 660 recommends a BiV pacing, if the LV lead is in an anterior position, then LV-only pacing is instead recommended.

Dynamic Stimulation Mode Switching Between SSP and MSP

Figure 7:
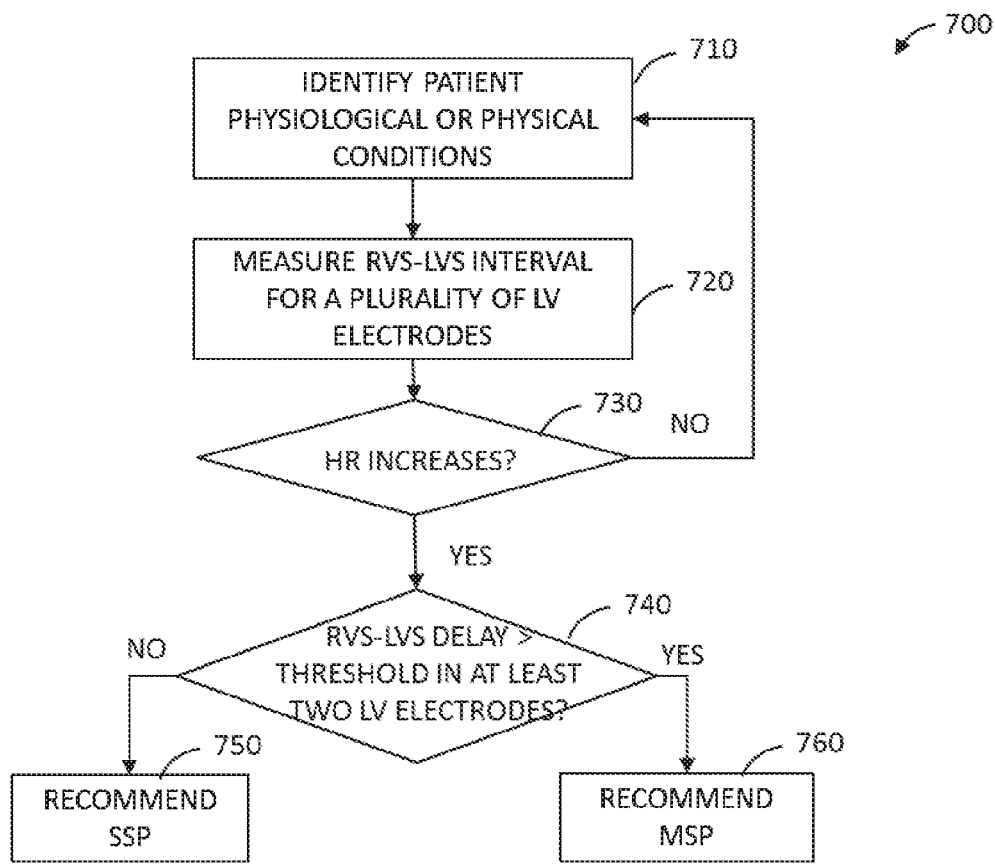
FIG. 7 illustrates an example of a method for determining between SSP pacing and MSP.

FIG. 7 illustrates an example of a method 700 for determining between SSP pacing and MSP. The method 700 may be implemented in and executed by the stimulation mode selector circuit 232 as illustrated in FIG. 2. In an example, the method 700 may be used to determine stimulation mode (SSP or MSP) on a beat-by-beat basis, or to adjust the stimulation site periodically at specified time.

The method 700 begins at 710 where the patient physiological or functional conditions are identified. Patient conditions, such as heart rate, patient posture, physical activity, atrial activation mode, among others, may have an impact on the hemodynamic outcome during SSP or MSP. At 720, inter-ventricular interval may be respectively measured at a plurality of candidate LV sites {LV(i)}. The resulting inter-ventricular intervals {D(i)} represent respectively degrees of dyssynchrony between RV and various LV sites {LV(i)}. In an example, RVS may be sensed using an RV sensing vector comprising one of the RV electrodes 152-154, and LVS may be sensed at two or more LV sites using sensing vectors that each comprise one of the LV electrode 161-164. The inter-ventricular interval may be computed as a difference between (1) the AS to RVS interval and (2) the AS to LVS interval. Alternatively, the inter-ventricular interval may be computed as a difference between (1) the AP to RVS interval and (2) the AP to LVS interval. For example, for a particular LV site LV(j), the corresponding inter-ventricular interval D (j)=$AV_R$−$AV_L$(j), where $AV_R$ denotes the delay between AS or AP to RVS, and the $AV_L$(j) denotes the delay between AS or AP to LVS sensed at j-th LV site LV(j). In an example, the $AV_R$ or $AV_L$ may be measured while maintaining the pacing therapy, such as using the method 500 based on pseudofusion detection.

At 730, a trigger event is detected. The trigger event may include a change in patient physiological or functional condition, such as a posture change, physical activity intensity change, or a chronic change in patient HF status such as a decompensation event. In an example, the trigger event includes an increase in heart rate. If X out of Y beats exceed a heart rate threshold, then a stimulation site assessment may be triggered. In an example, three out of five consecutive beats exceeding a rate cutoff of 100 bpm may trigger the stimulation mode assessment. Alternatively, stimulation mode assessment may be performed periodically at specified time.

If the heart rate criterion is satisfied at 730, then at 740 the stimulation mode assessment is triggered, and the inter-ventricular intervals {D(i)} corresponding to the LV sites {LV(i)} may each be compared to an inter-ventricular delay threshold $D_{TH}$. In an example, the threshold $D_{TH}$ may be determined for various patient conditions, such as using echocardiography data or other heart failure diagnostics. The threshold $D_{TH}$ may be patient condition dependent, such that the threshold $D_{TH}$ at one patient condition may be different from the $PRI_{TH}$ at another different patient condition. An LV site, such as LV(i), may be selected for delivering pacing if the corresponding inter-ventricular interval, D(i), exceeds the threshold $D_{TH}$. For example, because the threshold $D_{TH}$ is patient-indication dependent, an LV site LV(i) may be selected for prone posture, while a different LV site LV(j) may be selected for standing posture. If at 740, two or more LV sites satisfy the inter-ventricular interval criterion, then the LV electrodes at those LV sites are selected for delivering MSP at 760. If only one LV site satisfies the inter-ventricular interval criterion, then SSP using the LV electrode at that site is recommended at 750. If none of the LV sites satisfies the inter-ventricular interval criterion, then SSP is recommended at 750 using the LV electrode that corresponds to the longest inter-ventricular interval among the candidate LV sites {LV(i)}.

Non-Transient Machine Readable Medium

Figure 8:
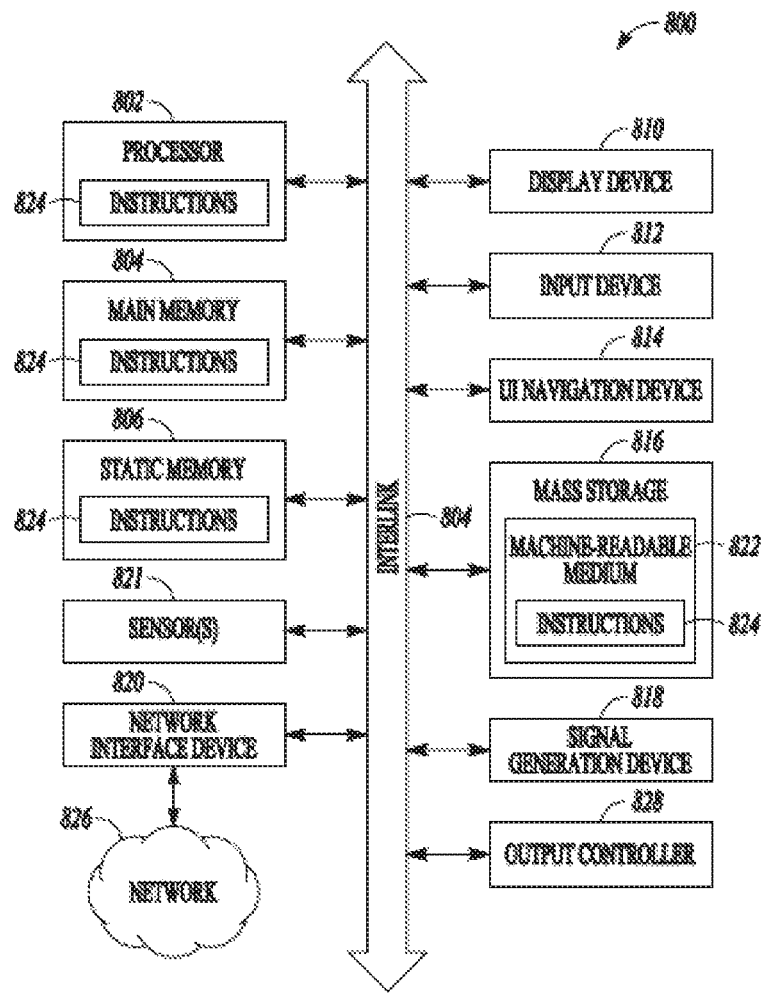
FIG. 8 illustrates a block diagram of an example machine upon which any one or more of the techniques (e.g., methodologies) discussed herein may perform.

FIG. 8 illustrates a block diagram of an example machine 800 upon which any one or more of the techniques (e.g., methodologies) discussed herein may perform. Portions of this description may apply to the computing framework of various portions of the LCP device, the IMD, or the external programmer.

In alternative embodiments, the machine 800 may operate as a standalone device or may be connected (e.g., networked) to other machines. In a networked deployment, the machine 800 may operate in the capacity of a server machine, a client machine, or both in server-client network environments. In an example, the machine 800 may act as a peer machine in peer-to-peer (P2P) (or other distributed) network environment. The machine 800 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

Examples, as described herein, may include, or may operate by, logic or a number of components, or mechanisms. Circuit sets are a collection of circuits implemented in tangible entities that include hardware (e.g., simple circuits, gates, logic, etc.). Circuit set membership may be flexible over time and underlying hardware variability. Circuit sets include members that may, alone or in combination, perform specified operations when operating. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

Machine (e.g., computer system) 800 may include a hardware processor 802 (e.g., a central processing unit (CPU), a graphics processing unit (GPU), a hardware processor core, or any combination thereof), a main memory 804 and a static memory 806, some or all of which may communicate with each other via an interlink (e.g., bus) 808. The machine 800 may further include a display unit 810 (e.g., a raster display, vector display, holographic display, etc.), an alphanumeric input device 812 (e.g., a keyboard), and a user interface (UI) navigation device 814 (e.g., a mouse). In an example, the display unit 810, input device 812 and UI navigation device 814 may be a touch screen display. The machine 800 may additionally include a storage device (e.g., drive unit) 816, a signal generation device 818 (e.g., a speaker), a network interface device 820, and one or more sensors 821, such as a global positioning system (GPS) sensor, compass, accelerometer, or other sensor. The machine 800 may include an output controller 828, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

The storage device 816 may include a machine readable medium 822 on which is stored one or more sets of data structures or instructions 824 (e.g., software) embodying or utilized by any one or more of the techniques or functions described herein. The instructions 824 may also reside, completely or at least partially, within the main memory 804, within static memory 806, or within the hardware processor 802 during execution thereof by the machine 800. In an example, one or any combination of the hardware processor 802, the main memory 804, the static memory 806, or the storage device 816 may constitute machine readable media.

While the machine readable medium 822 is illustrated as a single medium, the term "machine readable medium" may include a single medium or multiple media (e.g., a centralized or distributed database, and/or associated caches and servers) configured to store the one or more instructions 824.

The term "machine readable medium" may include any medium that is capable of storing, encoding, or carrying instructions for execution by the machine 800 and that cause the machine 800 to perform any one or more of the techniques of the present disclosure, or that is capable of storing, encoding or carrying data structures used by or associated with such instructions. Non-limiting machine readable medium examples may include solid-state memories, and optical and magnetic media. In an example, a massed machine readable medium comprises a machine readable medium with a plurality of particles having invariant (e.g., rest) mass. Accordingly, massed machine-readable media are not transitory propagating signals. Specific examples of massed machine readable media may include non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 824 may further be transmitted or received over a communications network 826 using a transmission medium via the network interface device 820 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as WiFi®, IEEE 802.16 family of standards known as WiMax®), IEEE 802.15.4 family of standards, peer-to-peer (P2P) networks, among others. In an example, the network interface device 820 may include one or more physical jacks (e.g., Ethernet, coaxial, or phone jacks) or one or more antennas to connect to the communications network 826. In an example, the network interface device 820 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 800, and includes digital or analog communications signals or other intangible medium to facilitate communication of such software.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

The invention claimed is:

1. A system, comprising:
a stimulation control circuit configured to:
store, in a memory, pacing site configuration information including a first pacing site configuration at first AV conduction characteristics respectively determined for a plurality of heart rates or heart rate ranges, and a second pacing site configuration at second AV conduction characteristics respectively determined for the plurality of heart rates or heart rate ranges;
receive a sensed heart rate of a patient; and
select one of the first pacing site configuration or the second pacing site configuration for delivering cardiac stimulation to the patient using a measured AV conduction characteristic of the patient and the sensed heart rate according to the stored pacing site configuration information.

2. The system of claim 1, wherein:
the sensed heart of the patient is a current heart rate of the patient;
the measured AV conduction characteristic includes an atrioventricular interval or an atrioventricular interval variability;
the first pacing site configuration includes left-ventricular (LV) only pacing and the second pacing site configuration includes a bi-ventricular (BiV) pacing of both left and right ventricles; and the cardiac stimulation control circuit is configured to periodically receive the measured AV conduction characteristic at a different frequency than the sensed heart rate, and to select one of the LV-only pacing or the BiV pacing according to an atrioventricular interval or an atrioventricular interval variability at the sensed heart rate.

3. The system of claim 2, wherein the cardiac stimulation control circuit is configured to select the BiV pacing when the atrioventricular interval exceeds a first threshold, or when the atrioventricular interval variability exceeds a second threshold.

4. The system of claim 2, wherein the cardiac stimulation control circuit is configured to select the LV-only pacing when the atrioventricular interval falls below a first threshold and the atrioventricular interval variability falls below a second threshold.

5. The system of claim 1, wherein the measured AV conduction characteristic includes a measured AV conduction characteristic for atrial sensed (AS) events and a measured AV conduction characteristic for atrial paced (AP) events, and the stimulation control circuit is configured to select one of the first pacing site configuration or the second pacing site configuration according to the measured AV conduction characteristic for an AS or AP event at the sensed heart rate.

6. The system of claim 5, wherein the stimulation control circuit is configured to store in the memory a stimulation parameter table that includes the first and second pacing site configurations for the AS and AP events and corresponding to the plurality of heart rates or heart rate ranges.

7. The system of claim 1, wherein the stimulation control circuit is configured to select the first pacing site configuration or the second pacing site configuration for delivering cardiac stimulation in response to an increase in heart rate.

8. A system, comprising:
a stimulation control circuit configured to:
store, in a memory, pacing site configuration information including a first pacing site configuration at first VV conduction characteristics respectively determined for a plurality of heart rates or heart rate ranges, and a second pacing site configuration at second VV conduction characteristics respectively determined for the plurality of heart rates or heart rate ranges;
receive a sensed heart rate of a patient; and
select one of the first pacing site configuration or the second pacing site configuration for delivering cardiac stimulation to the patient using a measured VV conduction characteristic of the patient and the sensed heart rate according to the stored pacing site configuration information.

9. The system of claim 8, wherein:
the sensed heart of the patient is a current heart rate of the patient;
the measured VV conduction characteristic includes an inter-ventricular interval;
the first pacing site configuration includes a single-site left ventricular pacing (SSP) and second pacing site configuration includes a multi-site left ventricular pacing (MSP) at two more left-ventricular sites; and
the cardiac stimulation control circuit is configured to periodically receive the measured VV conduction characteristic at a different frequency than the sensed heart rate, and to select the SSP or the MSP according to an inter-ventricular interval at the sensed heart rate.

10. The system of claim 9, wherein the cardiac stimulation control circuit is configured to measure inter-ventricular intervals between a right ventricular site and a plurality of left ventricular sites, and to select the SSP or the MSP based on a number of the plurality of left ventricular sites having the corresponding inter-ventricular intervals satisfying a condition.

11. The system of claim 10, wherein the cardiac stimulation control circuit is configured to select the MSP when at least two left-ventricular sites have respective inter-ventricular intervals exceeding an inter-ventricular interval threshold, and to select the SSP when no more than one left-ventricular site has an inter-ventricular interval exceeding an inter-ventricular interval threshold.

12. The system of claim 8, wherein the stimulation control circuit is configured to select the first pacing site configuration or the second pacing site configuration for delivering cardiac stimulation in response to an increase in heart rate.

13. A method of operating a system to control cardiac stimulation, the method comprising:
storing, in a memory, pacing site configuration information including a first pacing site configuration at first AV conduction characteristics respectively determined for a plurality of heart rates or heart rate ranges, and a second pacing site configuration at second AV conduction characteristics for the plurality of heart rates or heart rate ranges;
receiving a sensed heart rate of a patient; and
selecting one of the first pacing site configuration or the second pacing site configuration for delivering cardiac stimulation using a measured AV conduction characteristic of the patient and the sensed heart rate according to the stored pacing site configuration information.

14. The method of claim 13, wherein the first pacing site configuration includes left-ventricular (LV) only pacing and the second pacing site configuration includes a bi-ventricular (BiV) pacing of both left and right ventricles, and selecting one of the first or second pacing site includes selecting the LV-only pacing or the BiV pacing according to an atrioventricular interval or an atrioventricular interval variability at the sensed heart rate.

15. The method of claim 14, wherein selecting the first or second pacing site configuration includes:
selecting the BiV pacing when the atrioventricular interval exceeds a first threshold, or when the atrioventricular interval variability exceeds a second threshold; and
selecting the LV-only pacing when the atrioventricular interval falls below the first threshold, and when the atrioventricular interval variability falls below the second threshold.

16. The method of claim 13, wherein the measured AV conduction characteristic includes a measured AV conduction characteristic for atrial sensed (AS) events and a measured AV conduction characteristic for atrial paced (AP) events, and the selecting one of the first or second pacing site configuration is in accordance with the measured AV conduction characteristic for an AS or AP event at the sensed heart rate.

17. The method of claim 13, wherein the stored pacing site configuration information further includes a single-site left ventricular pacing (SSP) at first VV conduction characteristics respectively determined for the plurality of heart rates or heart rate ranges, and a multi-site left ventricular pacing (MSP) at second VV conduction characteristics for the plurality of heart rates or heart rate ranges, the method further comprising:
  selecting one of the (SSP) or the (MSP) using a measured VV conduction characteristic of the patient and the sensed heart rate according to the stored pacing site configuration information.

18. The method of claim 17, wherein the sensed heart of the patient is a current heart rate of the patient, the measured VV conduction characteristic includes inter-ventricular intervals between a right ventricular site and a plurality of left ventricular sites, and selecting the SSP or the MSP is based on a number of the plurality of left ventricular sites having the corresponding inter-ventricular intervals satisfying a condition.

19. The method of claim 18, wherein selecting between SSP and MSP includes:
  selecting the MSP when at least two left-ventricular sites have respective inter-ventricular intervals exceeding an inter-ventricular interval threshold; and
  selecting the SSP when no more than one left-ventricular site has an inter-ventricular interval exceeding the inter-ventricular interval threshold.

20. The method of claim 13, wherein selecting the first pacing site configuration or the second pacing site configuration for delivering cardiac stimulation is in response to an increase in heart rate.

* * * * *